(12) United States Patent
Kühnel-Sumann et al.

(10) Patent No.: US 12,295,809 B2
(45) Date of Patent: May 13, 2025

(54) DENTAL PROCEDURES

(71) Applicant: DENTSPLY SIRONA INC., York, PA (US)

(72) Inventors: Felix Kühnel-Sumann, Zürich (CH); Sascha Scandella, Zürich (CH); Thomas Fitze, Zürich (CH)

(73) Assignee: Dentsply Sirona Inc., York, PA (US)

( * ) Notice: Subject to any disclaimer, the term of this patent is extended or adjusted under 35 U.S.C. 154(b) by 770 days.

(21) Appl. No.: 17/395,689

(22) Filed: Aug. 6, 2021

(65) Prior Publication Data
US 2023/0038964 A1    Feb. 9, 2023

(51) Int. Cl.
*A61C 9/00*    (2006.01)
*A61B 34/10*    (2016.01)

(52) U.S. Cl.
CPC ............ *A61C 9/0046* (2013.01); *A61B 34/10* (2016.02); *A61B 2034/102* (2016.02); *A61B 2034/108* (2016.02)

(58) Field of Classification Search
CPC ....... A61C 9/0046; A61C 9/00; A61C 9/0006; A61C 9/004; A61B 34/10; A61B 2034/102; A61B 2034/108
See application file for complete search history.

(56) References Cited

U.S. PATENT DOCUMENTS

| | | | |
|---|---|---|---|
| 2012/0158002 A1* | 6/2012 | Carignan | A61F 2/461 606/89 |
| 2015/0265373 A1* | 9/2015 | Jamison | A61C 1/085 433/173 |
| 2020/0125069 A1* | 4/2020 | Sirovskiy | A61C 7/002 |
| 2020/0345455 A1* | 11/2020 | Roein Peikar | A61C 7/002 |
| 2020/0352736 A1* | 11/2020 | Van Rensburg | A61C 8/0089 |
| 2022/0054238 A1* | 2/2022 | Kim | A61C 1/084 |

* cited by examiner

*Primary Examiner* — Yogesh P Patel
(74) *Attorney, Agent, or Firm* — SCHWEGMAN LUNDBERG & WOESSNER, P.A.

(57) ABSTRACT

The present teachings relate to a method for processing a digital dental impression comprising: displaying an image of the digital dental impression; wherein the image comprises: a shaded region representative of a part of the oral anatomy which is relevant for a dental procedure, and the shaded region being enclosed within a boundary; and an unshaded region representative of a part of the oral anatomy which is not relevant for a dental procedure, wherein the unshaded region and the shaded region are separated from each another by the boundary, receiving user input for altering the shaded region and/or unshaded region; detecting completion of a stroke generated by the user input; altering, the shaded region and/or the unshaded region, in response to the stroke completion. The present teachings also relate to a method for processing digital three-dimensional shapes, a dental procedure assisting system, uses and computer software products.

9 Claims, 9 Drawing Sheets

7(A)

7(B)

DENTAL PROCEDURES

TECHNICAL FIELD

The present teachings relate generally to computer-implemented methods and products for assisting dented practitioners, for example in planning and performing, dental procedures such as restoration. More specifically, the present teachings relate to a user interface for dental procedure planning systems.

BACKGROUND

Dental procedures such as dental restorations are treatments that are used to restore, either one or more of, the function, integrity, or morphology of missing or damaged dental structure of a patient. Damage or loss of the dental structure or teeth may for example have occurred due to caries or external trauma. Dental restoration may also include replacement of such a structure, for example by dental implants. Computer-aided systems exist for design and/or manufacture of artificial dental structures. Accordingly, such replacement structures can be designed using a computer-aided design ("CAD") software, Frequently, a designed structure is then manufactured using a computer-aided manufacturing ("CAM") system.

Often, dental replacements such as crowns or bridges are attached at a desired oral anatomical location using one or more fixtures such as dental implants. Locating an appropriate location of the fixture can be of importance for a correct placement of the dental replacement. Template structures such as surgical guides are commonly used to help minimize guesswork during implant work. The templates such as surgical guides are designed to replicate the surfaces of the patient's intraoral anatomy and thus, they are designed to assist the dental practitioner to drill implants into the hone with desired accuracy. After placing the template on the patient's jaw, the practitioner can use sleeves of the template to help guide the surgical instruments to the proper location and thus achieve a proper placement of the implant. Such templates can be created by taking impressions of the patient's oral anatomy. The dental impression may be physical, or it may be a digital impression captured e.g., via an intraoral scan of the oral anatomy of the patient, e.g., the desired surgical implant site. There is often a possibility for the dental practitioner to make manual adjustments to the digital dental impression using a CAD system e.g., a computerized implant planning system. Such adjustments may include enlarging the template size in a particular direction, or it may even include reducing the size. These alterations can be done using a desktop computer connected to an input device each as a mouse or a trackball. More recently the use of touch-based user interfaces has become popular as it can allow the user more portability and convenience in use. A touch-based interface can also create challenges in making adjustments to a CAD layout as such adjustments may not be as finely done as compared to conventional input devices such as mice and/or trackballs. Furthermore, adjustments that can be done in a real-time manner may be more interactive for the dental practitioner. Such interactive adjustments can save time and provide more flexibility and ease of use for the dental practitioner to determine a dental, impression which can result in a suitable dental object. However, performing computation intensive processing of visual elements, especially 3D shapes, in a real-time manner can be a challenge.

The applicant has realized that there is a need of improved methods and products for assisting dental procedures.

SUMMARY

At least some of the limitations associated with the foregoing can be overcome by the subject matter of the accompanying independent claims. At least some of the additional advantageous alternatives Will be outlined in the dependent claims.

When viewed from a first perspective, there can be provided a computer-implemented method for processing a digital dental impression, the digital dental impression being representative of an oral anatomy, which method comprises:
 providing, at a memory location, the digital dental impression;
 displaying, via a display device, an image of the digital dental impression; wherein the image comprises:
  a shaded region, the shaded region being representative of a part of the oral anatomy which is relevant for a dental procedure, and the shaded region being enclosed within a boundary; and
  an unshaded region, the unshaded region being representative of a part of the oral anatomy which is not relevant for the dental procedure, wherein the unshaded region and the shaded region are separated from each another by the boundary,
 receiving, via an input interface, a user input for altering the shaded regions and/or unshaded region;
 detecting, via a trigger logic, completion of a stroke generated by the user input;
 altering, the shaded region and/or the unshaded region, in response to the stroke completion.

The applicant has realized that rather than continuously processing resource intensive algorithms, or waiting for the user to finish performing any edits to the shaded and/or unshaded regions, the trigger logic can be leveraged for triggering execution of certain algorithms just when it becomes necessary. Hence, when used in an interactive platform, such as a CAD system, a faster processing can be achieved such that the alteration of the shaded region and/or the unshaded region can be shown to the user with a faster frame rate as compared to conventional solutions. The trigger logic is triggered when a stroke completion is detected.

"Completion of a stroke" or "stroke completion" refers to an instance or occurrence during the progress of the stroke, when the stroke either intersects with itself, or it intersects the shaded region. Thus, the stroke completion can refer to either an intersection of the stroke with itself or it may be an intersection of the stroke with the shaded region. Preferably, the stroke completion is an intersection of the stroke with the shaded region at two different locations. More preferably, the enclosing stroke completion includes detecting formation of a fully enclosed region due to the stroke or in response to the stroke. Thus, preferably, the stroke completion is an "enclosed stroke completion" which forms an enclosed region. Detection of the completion of an enclosed region can further reduce the processing requirements by executing specific algorithms such as fill hole algorithm or erase island algorithm just when it may be needed.

For example, for detecting the enclosed region it may be detected if the enclosed region is completely formed by an edge of the stroke. Such a self-intersection of a stroke may occur when the leading end of the stroke meets or intersects any other part of the same stroke. For example, when the user draws a loop via the user input, the brush tip may meet its previously drawn trail thus forming a closed shape. By "leading"-end or -part, it is meant the most recently drawn end or part of the stroke. Thus, when looking at a completed stroke, the leading end would be the part of the stroke corresponding to where it ended, e.g., the point when the corresponding user input stopped, or the point where the user removed the brush or eraser from drawing. Rest of the portion of the stroke may be considered trailing part of the same stroke, i.e., the part where the stroke started and/or the part where the stroke was performed prior to arriving at the leading end. Those skilled in the art shall appreciate that these terms are herein used in a relative sense for the ease of understanding. The terms are thus not to be regarded as limiting to the scope or generality of the present teachings. Self-intersecting strokes may be used for forming, e.g., within the unshaded space, one or more shaded "islands" or isolated shaded regions.

Similarly, for detecting the enclosed region it may be detected if the enclosed region is completely formed by a portion of an edge of the stroke and a section of the boundary of the shaded region. This may happen when a brush stroke intersects the shaded region in at least two locations such that the enclosed region is formed between a part of the outline or perimeter of the stroke and a part of the boundary of the shaded region. Dependent upon whether the drawing is in a draw mode or it is in an erase mode, the enclosed region may either be a part of the unshaded region or it may be a part of the shaded region.

The term "stroke" as used herein refers to a computerized trace drawn in response to the user input. Hence, stroke as referred herein can be a stroke of a brush made when drawing a shape or a region, for example, of the shaded region, or it may be an erasing stroke made for erasing at least a part of the shaded region. A stroke may thus either initiate in the shaded region or in the unshaded region. Those skilled in the art shall appreciate that strokes can have a width or thickness, for example corresponding to a brush width or an eraser width selected by the user for drawing or erasing respectively. The stroke may even have a length which depends on the length drawn by the user via the user input. The length may be entirely straight, or it may be uneven or curved. Similarly, the stroke width may be constant over the length of the stroke, or it may vary at one or more locations along the length dependent, e.g., upon if the brush angle or eraser angle is varied during the stroke. The brush stroke may be shown with a color which is selected by the user to draw the shape. For example, when editing the shaded region, the brush stroke may have the same color as the shaded region, or a similar color as the shaded region. In some cases, for the user to be able to distinguish an ongoing brash stroke from a pre-drawn shape, e.g., the shaded region, the stroke may be provided a slightly different color or shade as compared to the pre-drawn shape. After the stroke is complete, it may be provided the same color as the pre-drawn shape, either as whole, or just to the part of the stroke which is considered valid.

It shall further be appreciated that a stroke having width and length shall have an outline or perimeter determined by the width and the length of the stroke. Thus, for understanding the outline can be visualized as a line encircling and containing the trail of the stroke. In terms of computation of visual elements, the outline may refer to a series of outermost pixels or the coordinates thereof of the stroke. Thus, the stroke can be visualized as being fully contained within the outline. Hence, width and length of the stroke or its specific part can also be determined using the outline of said pixels (e.g., by distance measurement between two points on the outline).

"Digital dental impression" refers to any suitable three-dimensional ("3D") model or dataset representing the oral anatomy e.g., dental structure. For example, the digital dental impression may be of an oral anatomy which is digitally represented by triangulated 3D point clouds or 3D surface mesh, e.g., a mesh that has neighborhood information to the adjacent points. Since the herein disclosed trigger-based approach is a geometric approach, it is not restricted to any specific kind of model or data structure. It shall be appreciated that aspects of the present teachings relate to a geometrical concept and does not need any specific kind of model or data structure to be described. A model or data structure is a mere computerized description that defines a way for the computer to be able to realize the computation of the aspects. But the geometric approach as described herein is in itself sufficient to describe the overarching concept. It means, any model or data structure that is suitable for computing the approach can be used to apply the inventive ideas described herein. The digital dental impression may be in the form of one or more datasets. Hence, the digital dental impression may either be in the form of a plurality of computerized images, for example, 3D scan data or 3D scan images or a plurality of digital photos, or it may be used to provide, or it may be capable of providing the plurality of computerized images. The digital dental impression may be provided at a memory location such as a database indicative of the dental geometry related to the patient. The digital dental impression may be generated via one or more measurements performed using any one or more imaging systems such as, an oral scanner such as a dental camera or an intraoral scanner and/or X-ray system, and/or CT system. Thus, in some cases, in case of dental situation, the digital dental impression may be recorded with the aid of the oral scanner. The recording may capture the dental structure from multiple views and/or depths, for example, any one or more of, an occlusal direction, a lingual direction and/or a labial direction. The digital dental impression may be in any suitable format, for example as a plurality of 2D representations of 3D objects, including but not limited to, depth map, pseudo-images based on facet information, or other multi-angle images, Some non-limiting examples of 3D representations of 3D objects include volumetric representations, point clouds, primitive-based models, or meshes.

Virtual models such as the digital dental impression can enable the practitioner to study the restoration and/or the intra oral cavity of individual patients via a computer system, in a similar manner as traditional physical plaster model. A 3D model of the intra oral cavity can also allow the practitioner to study methods or approaches when dealing with particular dental problems of a patient. The model may also be used for the design of physical entities, such as prostheses, dental brackets, aligners and so on, e.g., to remedy the dental problems. For example, in prosthodontics, a 3D model of a patient's teeth may be used for providing machining data to manufacture a physical model of the intra oral cavity, and/or to design and manufacture a coping and/or a prosthesis, while in orthodontics the 3D model of a patient's teeth may be manipulated to enable a dental appliance, for example orthodontic brackets and/or aligners, to be desired and manufactured, and/or for designing a treatment.

The term "dental structure" refers to any one or more three-dimensional objects or intraoral geometries related to the oral anatomy, natural and/or man-made. The term may thus include any one or more physical objects such as dentition, dental restorations, their replacements, and such. As a few non-limiting examples, the dental structure may refer to one or more teeth and/or the immediate surroundings of a restoration to be inserted, and/or even a larger area in the oral cavity around the restoration to be inserted and/or the restoration itself. Hence, the dental structure may be a dental situation, or it may be a dental restoration, or even their combination.

"Input interface" may be a hardware and/or software interface via which the user input is received. Accordingly, the input interface may be a part of a human machine interface ("HMI"). The input interface hence may for example be in the form of a computer mouse, a trackball, a graphics tablet, a touch sensitive surface, or even a combination of one or more of these or other suitable devices for registering and/or receiving user input.

"Display device" refers to any device capable of visually displaying one or more perspective views of the digital dental impression, for example in the form of one or more images or as video. Accordingly, the display device may be a computer screen such as a monitor with CRT, LCD, LED, or OLED screen. In some cases, the display device may even be, or it may comprise an augmented reality ("AR") unit. In some cases, the display device may be a part of the HMI. The display device may comprise one or more computing units and/or the display device may be connectable to one or more computing units in a wired and/or wireless manner. The display device may even be part of a computing unit, for example, the display device may be a screen of a mobile device such as a tablet computer or a smartphone. In such cases, the input interface may comprise the touch sensitive surface of the mobile device. It shall thus be appreciated that in some cases, the input interface and the display device may be parts of the same unit.

"Shaded region" refers to a geometrical shape or region which is relevant for a dental procedure, for example the region which is to be included in a dental procedure or object. For example, the shaded region may represent an area of the dental region over which a surgical guide shall be placed. Additionally, or alternatively, the shaded region may represent a region in which a particular dental procedure is to be performed, for example, polishing of a dental crown. In such cases, once the dental practitioner or user provides a final confirmation, the dental procedure may be performed automatically on the dental region corresponding to the selected region. The shaded region may be of a regular shape or it may have an irregular shape. It shall be appreciated that the shaded region especially in context of 3D shapes such as dental geometries is in most cases a 3D geometry as well. In some cases, the image may even comprise a plurality of shaded regions separated from each another. Such separated shaded regions may correspond to the same dental procedure or object, or separate ones. Each of the shaded regions may be enclosed or contained within a boundary, e.g., a boundary region or a line of regular or irregular shape.

From the above, it shall be appreciated that "unshaded region" refers to a geometrical shape or region which is not relevant for a dental procedure or object, for example the region which is not to be included in a dental procedure. For example, the unshaded region may represent an area of the dental region which a surgical guide shall not cover. Additionally, or alternatively, the unshaded region may represent a region in which a particular dental procedure is to be avoided, for example, area which is not to be polished or cleaned. The unshaded region is separated from the shaded region via the boundary of the shaded region. If there are a plurality of shaded regions, then the unshaded region is separated via the boundary of each shaded region from the respective shaded region. The shaded region and the unshaded region can thus be considered mutually exclusive of each another.

One or more shaded regions may be included in the provided digital dental impression, e.g., as tag or annotation data, or the shaded region may have been generated after loading the dental impression in the memory location. For example, in some cases initially, the digital dental impression may not comprise any shaded region at all. The shaded region may thus have been added either manually by the user and/or it may have been at least partially automatically generated. Auto generation may involve a computing unit automatically recognizing features from the digital dental impression and automatically marking the shaded region. In some cases, the user may have edited the shaded region prior to or after auto generation.

"Dental procedure" refers to a procedure that needs to be performed, for example on parts of the oral anatomy. As non-limiting examples, the dental procedure may be any one or more of, milling, grinding, polishing and printing. In some cases, the dental procedure may be any manufacturing or machining procedure, e.g., related to a dental restoration. In some cases, the dental procedure may be, or it may comprise, a digital dental procedure, e.g. one or more preprocessing and/or selection steps to define the input for a specific algorithm or to mark certain parts of interest on the dental geometry, that will then be processed later in software.

According to an aspect, for performing the dental procedure and/or for producing the dental object, the method may comprise selecting at least partially automatically a tool. The term "tool" or more specifically "machining tool" may be used herein interchangeably to include any tool that is adapted for material removal, and may include inter ilia mechanical tools such as chamfers, grinders or drills for example, laser tools such as for example laser drills or cutters, ultrasonic tools such as for example ultrasonic cutters, and the likes. In some cases, the machining paths and material removal characteristics of such tools can be controlled, for example, by computer systems or other automated means.

In some cases, the dental object such as a replacement or restoration can be fully automatically produced from a blank by means of a CAM grinding machine using the dental procedure in response to the processed digital dental impression. Additionally, or alternatively, other techniques such as additive manufacturing may be used. This can have an advantage that the dental object can be produced ally automatically without user intervention or interaction.

By "altering the shaded region" it is meant expanding the shaded region or shrinking the shaded region. For example, the stroke may be drawn to extend the shaded region in a particular direction, or the stoke may be made to erase a part of the shaded region.

By "altering the unshaded region" it is meant drawing a new shaded region such that the unshaded region is shrunk by the same magnitude as occupied by the new shaded region. Additionally, or alternatively, "altering" of the unshaded region may also mean shrinking or extending of the unshaded region due to expanding or shrinking respectively of the shaded region.

More preferably, the altering of the shaded region and/or the unshaded region comprises automatically filling a fully enclosed region formed at least partially by the stroke. Also preferably, the altering of the shaded region and/or the unshaded region comprises automatically removing fill from the enclosed region formed in combination of a section of the boundary and a part of the outline of the stroke. This can for example be used for performing an erase operation for shrinking the shaded region.

It shall thus be appreciated that the trigger-based approach is used for executing a fill holes algorithm only in the case that a completion is necessary, for example when the stroke completion occurs or preferably when it indicates that an enclosed region is present. Any suitable algorithm for filling holes may be used for filling the enclosed region or space, for example, span filling. In this way, time-intensive computations are only performed when they are needed. This makes the present teachings particularly useful for a more interactive filling operation. The applicant has found that using the present teachings filling or removing thereof can be performed even while the user is still drawing, e.g., the user is still drawing the stroke. The filling algorithm waits far the stroke completion signal, in response to which filling is made and it can even be shown to the user to allow them to appreciate how the extended or shrunk portion of the shaded portion will look like. This can be done even while the user is still in a draw mode or erase mode respectively. If not satisfied, the user may abandon the stroke and try a different stroke. Thus, significant delay in post processing the filling of the holes or removal of the islands of shaded region can be avoided. This can also speed up the overall speed of a dental CAD/CAM appreciably.

Since the uses can appreciate the outcome in a more real-time manner, User friendliness Can also be improved, and redrawing time minimized. Especially for 3D structures where fill and removal also happen usually in a 3D space, this can create more flexibility for the user to by out different strokes without severely affecting the processing time. Accordingly, an overall quality of the dental procedure and/or a dental object produced the basis of the processing can also be improved. Now-a-days, some dental practitioners or technicians may prefer to work with touchscreen based systems such as a computer tablet, e.g., due to portability. Touch based inputs tend to be less precise as compared to other input forms such as mouse input. By automatically altering the shaded region and/or the unshaded region in response to the stroke completion, the present teachings can compensate for some of the disadvantages that the user encounters in CAD by use of a touchscreen. Especially, by autofill and erase of enclosed regions, the present teachings can make touchscreen interface more suitable also for 3D applications such as dental CAD applications. Another advantage of automatic filling as proposed is that validly detected enclosed regions as proposed are filled or erased automatically without user intervention, thus the number of strokes required can be reduced and work can be simplified.

Those skilled in the art shall appreciate that the steps e.g., receiving, detecting, altering and displaying may be repeated especially while the user is editing the shaded region and/or unshaded region.

In an alternate but related form there can also be provided, a computer-implemented method for processing, a digital dental impression, the digital dental impression being representative of an oral anatomy, which method comprises:

providing, at a memory location, the digital dental impression;

displaying, via a display device, an image of the digital dental impression; a herein the image comprises:
a shaded region, the shaded region being representative of a part of the oral anatomy which is relevant for a dental procedure, and the shaded region being enclosed within a boundary; and
an unshaded region, the unshaded region being representative of a part of the oral anatomy which is not relevant for the dental procedure, Wherein the unshaded region and the shaded region are separated from each another by the boundary, receiving, via an input interface, a user input for altering the shaded region and/or unshaded region;

detecting, via a trigger logic, a transition of the user input between the shaded region and the unshaded region;

altering, the shaded and/or unshaded region, in response to the transition which crosses the boundary at least twice.

By "transition" it is meant trail or movement of the stroke. More specifically, it is meant the outline of the stroke which intersects the boundary of the shaded region.

According to an aspect, the method may also comprise:
generating a processed digital dental impression based upon the digital dental impression, the processed digital dental impression including information of the altered shaded region and/or the altered unshaded region.

Thus, the processed digital dental impression may be generated and provided e.g., to the same or another memory location. The processed digital dental impression is provided information related to the altered shaded region and/or the altered unshaded region, for example, in the form of tag and/or annotation data. The data may be referenced to the digital dental impression. The processed digital dental impression may be used for saving the progress of the edits e.g., for completing the work at a later time, or the processed digital dental impression may be usable for performing a dental procedure and/or for producing a dental object.

Thus, the method may also comprise:
performing, using the processed digital dental impression, a dental procedure.

The digital dental impression may be used for guiding the user or dental practitioner for performing the dental procedure, and/or the dental procedure may be performed at least partially automatically.

Alternatively, or in addition, the method may also comprise:
manufacturing the processed digital dental impression, a dental object.

The digital dental impression may be used for guiding the user for producing the dental object and/or the dental object may be produced at least partially automatically. For example, the shaded region may be used by a milling machine and/or a grinder to produce a dental object from a blank, and/or it may be used to produce a mold for producing the dental object by a molding process. According to an aspect, the dental object is a surgical guide. According to another aspect, the dental object is a crown. According to another aspect, the dental object is a bridge. According to yet another aspect, the dental object is an aligner. According to another aspect, the dental object is a dental guard. According to another aspect, the dental object is an occlusal splint.

As previously discussed, according to an aspect the stroke completion comprises generating an intersection signal when a stroke, e.g., a brush stroke, intersects with itself. The brush stroke is a stroke for drawing one or more shaded regions. Thus, the trigger logic generates the intersection signal when it detects that the stroke intersected with its own body. This in be done, e.g., by detecting if one or more points along the outline of the stroke coincide, or it may be done by detecting formation of a second outline of the stroke.

According to another aspect, the stroke completion comprises generating, an intersection signal when a stroke intersects with the shaded region. This can be done, e.g., by detecting if one or more points along the outline of the stroke coincide and/or lie inside the Shaded region. More preferably, the second intersection signal indicating the second intersection with the shaded region is generated when the same stroke intersects the shaded region at least twice. According to another aspect, the intersection signal is generated when the same stroke intersects the shaded region at least twice.

According to an aspect, the stroke completion comprises detecting formation of an enclosed region. The detection of an enclosed region may be triggered in response to the intersection signal, e.g., self-intersection of a stroke, or an intersection between a stroke and a shaded region. An advantage of detecting the enclosed region can be that execution of algorithm such as a fill hole algorithm or erase island algorithm can be prevented if there is no enclosed region detected. The efficiency of computation can thus be improved.

A further advantage of using the intersection signal as a trigger for detecting the enclosed region can be that detection of enclosed region can be avoided unless it is really needed, thus further making the computation process more efficient.

In case of intersection between the stroke and the shaded region, the generation of the second intersection signal, or the generation of the intersection signal when the same stroke intersects the shade region at least twice can be further used to avoid detection of the enclosed region unless it is really needed.

In case of self-intersection, the enclosed region detection may involve determining if a fully enclosed region is framed by an edge of the stroke. For example, if a stroke loops back to its own body, it may encircle region which becomes enclosed within the inner edge of the stroke. The trigger logic may detect formation of such inner edge or outline for determining formation of the enclosed region. In case of a brush stroke in the unshaded region, the detection of the enclosed region may trigger alteration of the enclosed region from unshaded to a shaded region, e.g., color of the brush. The filling may thus be automatically done without user intervention and just when it is required. As it was discussed, such self-intersecting strokes may be used for forming islands of shaded regions. In some cases, the stroke may be an erasing stroke used for removing a shaded island. In this case a self-intersecting stroke and/or the enclosed region detection is used to automatically make the enclosed region unshaded, thereby erasing any island of shaded region lying within the enclosed region. Once an enclosed region is detected, a new boundary for the enclosed region may be evaluated or created. This may involve evaluating the pixels or data points that contain the enclosed region. A filling or erasure can thus be applied for the enclosed region confined to the new boundary. Thus, the enclosed region is in a way defined by the new boundary.

According to an aspect, the detection of enclosed region involves measurement of a section length or distance of the boundary between two intersection points. It shall be appreciated that the detection of the enclosed region as disclosed herein is also novel and inventive in its own right.

More specifically, the measurement is performed between intersection points belonging to the same intersection pair. This involves determining at least one intersection pair, each intersection pair having two intersection points, and then measuring the distance between the intersection points of each intersection pair. An enclosed region is detected when the distance "d" of one of the intersection pairs meets the criteria as, or similar to, outlined in equation (1).

$$d \le \frac{L}{x} \quad (1)$$

where, $$d = \begin{cases} d_{o \to i}, & \text{if section determination direction} \ne \text{the first direction} \\ d_{i \to o}, & \text{if section determination direction} = \text{the first direction} \end{cases} \quad (2)$$

In equation (1), d is the distance of an intersection pair, L is the total length or perimeter of the boundary of the shaded region with which the stoke intersected, and x is a predetermined number representing what fraction or % the distance d should be of the total length L. The total length L of the shaded region may for example be determined by calculating the circumference of the shaded region. The length can be measured by starting from any point on the boundary or boundary line in either clockwise or counterclockwise direction and counting the geometric distance until reaching the same point after covering the entire boundary.

The detection of enclosed region may, for example, be based on that distance d is 30%, around 30% or below, of the length L, in which case x may be 3.33 or around that value. Hence, if measured distance is lower than 30% of value of L, an enclosed region is detected. The value of x is provided as a non-limiting example, and in a relative sense. The persons skilled in the art shall appreciate that other equivalent criteria, which also meets the above-mentioned criteria may also be used. Similarly, x may be 2 or 2.5 or 3 or 4 or 4.5 or 5 in some cases. It shall be appreciated that distance d is measured along the boundary of the shaded region.

In addition to the above, the formation of intersection pairs and measurement of d is performed in such a manner that it also allows rejection of cases where no enclosed region is detected which needs to be filled or erased. This is achieved by meeting the criteria exemplified in (2).

For detecting enclosed space for a brash stroke intersecting with a shaded region, i.e., detecting enclosed region of unshaded region, the intersection pairs are formed by starting from an outgoing edge of the outline of the brush in a first direction. As it was explained, a stroke can be visualized as having an outline or perimeter. The outline can be measured by starting from any point on the outline in either clockwise or counterclockwise direction and counting the distance until reaching the same point after covering the entire outline. Hence, the first direction can either be clockwise or it can be counterclockwise direction. An outgoing edge or intersection would be an intersection at which one leaves the shaded region to enter the unshaded region when moving along the outline in the first direction. Similarly, an incoming edge or intersection would be an intersection at which one leaves the unshaded region to enter the shaded region when mowing along the outline in the first direction. So, for example, for forming the intersection pans or edge pairs, any outgoing edge can be used as a first intersection point of a first intersection pair. Then moving along the first direction, the adjacent intersection point will be an incoming intersection or edge, this adjacent point becomes the second intersection point of the first edge pair. Similarly, still moving along the same direction, the next intersection point, if it exists different from the points in the first edge pair, will be an outgoing edge which can be used as a first intersection point of a second intersection pair. Similarly, the further point in the same direction will be an incoming edge which can become the second intersection point of the second intersection pair.

For determining the distance d for each intersection pair, criteria (2) is applied. For this section determination direction is defined as the direction in which distance d is to be measured along the boundary of the shaded region. If the section determination direction is the same as the first direction, distance d for each pair is measured starting from their incoming intersection until their outgoing intersection point. If, however, the section determination direction is the opposite of the first direction, distance d for each pair is measured starting from their outgoing intersection until their incoming intersection point. If any of the distances meet the criteria of equation (1), enclosed region is detected between the section length lying between the corresponding pair and the part of the outline lying between the points of the same pair.

Those skilled in the art shall appreciate that the above criteria can be implemented in a simpler form in practice as will be shown in the examples in the present teachings. The criteria herein are thus shown in a sense that any variation of the implementation which satisfied the herein shown criteria is to be deemed to be lying within the scope of the present teachings. As some examples, the first direction may be a clockwise direction while the section determination direction is counterclockwise, or vice versa. Similarly, both the first direction and the section determination direction may be clockwise, they may both be counterclockwise. So, either of these examples can be implemented such that they satisfy the herein laid out criteria rather than implementing equations (1) and (2) directly as software instructions.

Similarly, an outgoing edge or intersection is called so in a relative sense, it may also be called a negative (−, or −ve) edge or intersection. Also, an incoming edge or intersection is called so in a relative sense, it may also be called a positive (+, or +ve) edge or intersection. They may also be called the opposite, without diverting from the spirit of the teachings.

An advantage of the approach that meets the above criteria is that for single tap or in cases where no enclosed space is created, a fill hole algorithm can be prevented from executing.

As it will be shown, for example, in a brush mode for an intersection that created an enclosed region within an already shaded region, no enclosed region will be detected. Detection of valid enclosed regions can thus be improved.

Accordingly, when the enclosed space or a valid enclosed space is detected, an altering step can be performed automatically.

The criteria applied in an erase mode is similar, but slightly different from the brush or draw mode as discussed above.

In an erase mode, similar to the brush mode, the measurement is performed between intersection points belonging to the same intersection pair. This involves determining at least one intersection pair, each intersection pair having two intersection points, and then measuring the distance between the intersection points of each intersection pair. An enclosed region is detected when the distance d of one of the intersection pairs meets the criteria as, or similar to, outlined in equation (1).

A slight variation in an erase mode relative to the brush mode is that for applying the same criteria (2), in erase mode the intersection pairs or edge pairs are formed by any incoming edge (instead of an outgoing edge) as a first intersection point of a first intersection pair. Then moving along the first direction, the adjacent or consecutive intersection point will be an outgoing intersection or edge, this adjacent point becomes the second intersection point of the first edge pair. Similarly, still moving along the same direction, the next intersection point, if it exists different from the points in the first edge pair, will be an incoming edge which can be used as a first intersection point of a second intersection pair. Similarly, the further point in the same direction will be an outgoing edge which can become the second intersection point of the second intersection pair. Thus, for determining the distance d for each intersection pair, the criteria (2) can be applied.

Those skilled in the art shall appreciate that the above is a way to apply the same criteria for draw and erase strokes which intersect a shade region. Variations may be possible, e.g., by defining different criteria for the draw mode and the erase mode. Hence, as mentioned for the draw case, the criteria herein are thus shown in a sense that any variation of the implementation which satisfied the herein shown criteria is to be deemed to be lying within the scope of the present teachings.

The method steps disclosed herein may be performed by one or more computing units. At least one of the computing units may be operatively connected to the memory location.

When viewed from another perspective, there can also be provided a system for assisting a dental procedure, wherein the system is configured to perform any of the methods herein disclosed. For example, there can be provided a system comprising one or more computing units configured to perform any of the methods herein disclosed.

For example, there can be provided dental procedure assisting system, wherein the system is configured to:
  operatively connect to a memory location for obtaining a digital dental impression, wherein the digital dental, impression is representative of an oral anatomy;
  display, via a display device, an image of the digital dental impression; wherein the image comprises:
    a shaded region, the shaded region being representative of a part of the oral anatomy which is relevant for a dental procedure, and the shaded region being enclosed within a boundary; and
    an unshaded region, the unshaded region being representative of a part of the oral anatomy which is not relevant for a dental procedure, wherein the unshaded region and the shaded region are separated from each another by the boundary;
  receive, via an input interface, a user input for altering the shaded region and/or unshaded region;
  detect, via a trigger logic, completion of a stroke generated by the user input;
  alter, the shaded region and/or the unshaded region, in response to the stroke completion.

Any of the systems herein disclosed may comprise one or more computing units. Optionally, any of the systems and/or any of the computing units may be configured to operatively connect to a network, e.g., via one or more network interfaces and/or connectivity interfaces.

The memory location may be a part of a computing unit and/or the system, or it may be located remotely operatively accessible via any of the computing units.

As it was discussed, the methods and systems for detecting enclosed region are inventive in their own right, thus when viewed from another perspective there can also be provided a method for processing digital three-dimensional shapes, specifically digital anatomical shapes, which method comprises:

detecting, via one or more computing units, completion of a stroke; wherein the completion of the stroke involves forming of an enclosed region confined at least partially within an outline of the stroke, evaluate, via any one or more of the computing units, a new boundary around the enclosed region; the new boundary including the outline, alter, via any one or more of the computing units, properties of the enclosed region.

The enclosed region may be formed partially confined by a section of a boundary which separates a shaded region from an unshaded region. The enclosed region is thus confined within the section and the outline. The new boundary in this case also includes the section. The method may also include displaying via a display device any one or more, preferably all, of: the stroke, the enclosed region, the boundary, the new boundary, and the alteration. The alternatives and features discussed for methods and systems for processing can be applied here as well.

In an alternate but related form, there can also be provided a method for processing digital three-dimensional shapes, specifically digital anatomical shapes, which method comprises:

detecting, via one or more computing units, intersection of a drawing stroke at a boundary at two different locations of the boundary; wherein the boundary separates a shaded region from an unshaded region, detecting, via any one or more of the computing units, an enclosed region formed by the drawing stroke and the section of the boundary between the two intersection locations, altering, via any one or chore of the computing units, properties of the shaded region.

From a system point of view when viewed from another perspective there can also be provided a trigger logic for processing digital three-dimensional shapes, specifically digital anatomical shapes, wherein the logic is configured to:

detect completion of a stroke; wherein the completion of the stroke involves forming of an enclosed region confined at least partially within an outline of the stroke, evaluate a new boundary around the enclosed region; the new boundary including the outline, alter properties of the enclosed region.

As it was discussed, the enclosed region may be formed partially confined by a section of a boundary which separates a shaded region from an unshaded region. The enclosed region is thus confined within the section and the outline. The new boundary in this case also includes the section.

In an alternate but related form, there can also be provided a trigger logic for processing digital three-dimensional shapes, specifically digital anatomical shapes, wherein the logic is configured to:

detect intersection of a drawing stroke at a boundary at two different locations of the boundary; wherein the boundary separates a shaded region from an unshaded region, detect an enclosed region formed by the drawing stroke and the section of the boundary between the two intersection locations, alter properties of the shaded region.

The trigger logic may, for example, be in hardware and/or software form. The trigger logic may even be in the form of a computer software medium, e.g., a computer-readable storage medium or a non-transitory computer-readable storage medium storing the trigger logic.

When viewed from another perspective, there can also be provided a computer software product, or a non-transitory computer-readable storage medium storing the program, comprising instructions which when executed by a suitable computing unit cause the computing unit to perform any of the methods herein disclosed.

For example, there can be provided a computer software product, or a non-transitory computer-readable storage medium storing the program, comprising instructions which when executed by suitable one or more computing units cause any one or more of the computing units to:

operatively connect to a memory location for obtaining a digital dental impression, wherein the digital dental impression is representative of an oral anatomy;

display, via a display device, an image of the digital dental impression; wherein the image comprises:
a shaded region, the shaded region being representative of a part of the oral anatomy which is relevant for a dental procedure, and the shaded region being enclosed within a boundary; and
an unshaded region, the unshaded region being representative of a part of the oral anatomy which is not relevant for a dental procedure, wherein the unshaded region and the shaded region are separated from each another by the boundary;

receive, via an input interface, a user input for altering the shaded region aid/or unshaded region;

detect, via a trigger logic, completion of a stroke generated by the user input alter, the shaded region and/or the unshaded region, in response to the stroke completion.

A computer-readable data medium or carrier includes any suitable data storage device on which one or more sets of instructions (or software) are stored for implementing any one or more methodologies disclosed herein. The instructions may even reside partially, or completely, within the main memory and/or within the processor dining execution thereof by the processing unit, computing unit, and main memory, which may constitute computer-readable storage media. The instructions may even be transmitted or received over a network via a network device.

The computer program for implementing one or more of the aspects described herein may be stored and/or distributed on a suitable medium, such as an optical storage medium or a solid state medium supplied together with or as a part of another hardware, but may also be distributed in other forms, such as via the Internet or other wired or wireless telecommunication systems. However, the computer program may also be presented over a network like the World Wide Web and can be downloaded into the working memory of a data processor from such a network.

Furthermore, data carrier or a data storage medium for making a computer program product available for downloading can also be provided, which computer program product is arranged to perform a method according to any of the methods herein disclosed.

When viewed from another perspective, there can also be provided a computing unit comprising the computer program code for performing the method herein disclosed. Also, there can be provided a computing unit operatively coupled to a memory storage comprising the computer program code for carrying out any of the methods herein disclosed.

When viewed from another perspective, there can also be provided a use of the processed digital dental impression as generated pursuant to the herein disclosed methods for producing a dental object.

When viewed from another perspective, there can also be provided a data storage medium storing the processed digital dental impression as generated pursuant to the herein disclosed methods.

That two or more components are "operatively" coupled or connected shall be clear to those skilled in the art. In a non-limiting manner, this means that there may be at least one communicative connection between the coupled or connected components e.g., they are the network interface or any suitable interface. The communicative connection may either be fixed, or it may be removable. Moreover, the communicative connection may either be unidirectional, or it may be bidirectional. Furthermore, the communicative connection may be wired and/or wireless. In some cases, the communicative connection may also be used for providing control signals.

"Processing unit" or "computing unit" may comprise, or it may be, a processing means or computer processor such as a microprocessor, microcontroller, or the likes, having one or more computer processing cores.

"Computer processor" refers to an arbitrary logic circuitry configured for performing basic operations of a computer or system, and/or, generally, to a device which is configured for performing calculations or operations. In particular, the processing means or computer processor may be configured for processing basic instructions that drive the computer or system. As an example, the processing means or computer processor may comprise at least one arithmetic logic unit ("ALU"), at least one floating point unit ("FPU"), such as a math coprocessor or a numeric coprocessor, a plurality of registers, specifically registers configured for supplying operands to the ALU and storing results of operations, and a memory such as an L1 and L2 cache memory. In particular, the processing means or computer processor may be a multi core processor. Specifically, the processing means or computer processor may be or may comprise a central processing unit ("CPU"), the processing means or computer processor may be a complex instruction set computing ("CISC") microprocessor, reduced instruction set computing microprocessor ("RISC"). Very long instruction word ("VLIW") microprocessor, a processor implementing other instruction sets or processors implementing a combination of instruction sets. The processing means may also be one or more special purpose processing devices such as an application specific integrated circuit ("ASIC"), a field programmable gate array ("FPGA"), a complex programmable logic device ("CPLD"), a digital signal processor ("DSP"), in next word processor, or the like. The methods, systems and devices disclosed herein may be implemented as software in a DSP, in a microcontroller, or in any other side processor such as hardware unit within an ASIC, CPLD, or FPGA. It is to be understood that the term processing means or processor may also refer to one or more processing devices, such as a distributed system of processing devices located across multiple computer systems (such as cloud computing), and is not limited to a single device unless otherwise specified.

"Connectivity interface" refers to a software and/or hardware interface for establishing communication such as transfer or exchange of signals or data. The communication may either be wired, or it may be wireless. Connectivity interface is preferably based on or it supports one or more communication protocols. The communication protocol may be a wireless protocol, for example: short distance communication protocol such as Bluetooth®, or Wi-Fi, or long communication protocols such as cellular or mobile network, for example, second generation cellular network ("2G"), 3G, 4G, long term evolution ("LTE"), or 5G. Alternatively, or in addition, the connectivity interface may even be based on proprietary short distance or long distance protocol. The connectivity interface may support any one or more standards and/or proprietary protocols.

"Network interface" refers to a device or a group of one or more hardware and/or software components that allow an operative connection with the network.

"Memory storage" may refer to a device for storage of information, in the form of data, in a suitable storage medium. Preferably, the memory storage is a digital storage suitable for storing the information in a digital form which is machine readable, for example digital data that are readable via a computer processor. The memory storage may thus be realized as a digital memory storage device that is readable by a computer processor. Further preferably, the memory storage on the digital memory storage device may also be manipulated by a computer processor. For example, any part of the data recorded on the digital memory storage device may be written and or erased and or overwritten, partially or wholly, with the new data by the computer processor.

"Network" discussed herein may be any suitable kind of data transmission medium, wired, wireless, or their combination. A specific kind of network is not limiting to the scope or generality of the present teachings. The network can hence refer to any suitable arbitrary interconnection between at least one communication end point to another communication end point. Network may comprise one or more distribution points, routers or other types of communication hardware. The interconnection of the network may be formed by means of physically hard wiring, optical and/or wireless radio frequency ("RF") methods. The network specifically may be, or it may comprise, a physical network fully or partially made by hard wiring, such as a fiber optical network or a network frilly or partially made by electrically conductive cables or a combination thereof. The network may at least partially comprise the Internet.

DETAILED DESCRIPTION

Certain aspects of the present teachings will now be discussed with reference to the accompanying drawings that explain said aspects by the way of examples. Since the generality of the present teachings is not dependent on it, the drawings may not be to scale. Method and system aspects may be discussed in conjunction for ease of understanding. Certain features shown in the drawings may be local features that are shown together with physical features for the sake of understanding and without affecting the generality or scope of the present teachings.

Figure 1:
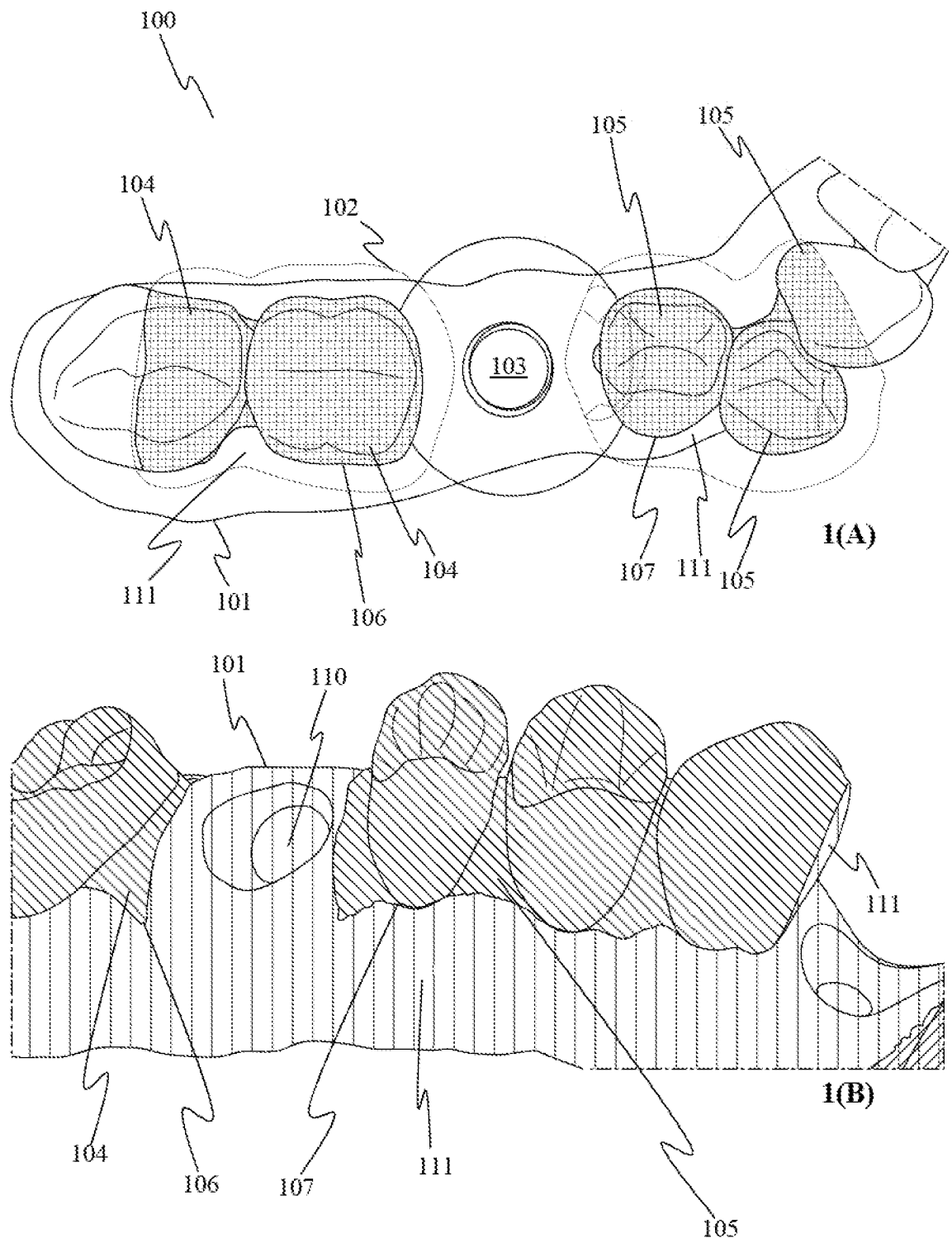
FIG. 1 illustrates an example of a surgical guide.

The reference numbers shown in the drawings denote the elements which will be referred to in the subsequent description of the examples of the present teachings:

In accordance with example aspects described herein, methods, systems and computer readable storage media can be provided, e.g., for assisting a dental scan.

FIG. 1 illustrates views 100 of a digital dental impression. More particularly view 1(A) shows a top view of a portion of the digital dental impression, which represents a three-dimensional portion of a patient's oral anatomy, more specifically a portion of the patient's jaw 101. Each of the views 1(A) and 1(B) may represent an image which is displayed via a display device for a user such as a dental practitioner or technician. The views 1(A) and 1(B) thus may be provided by a CAD program for example for designing a dental object such as a surgical guide 102. The surgical guide 102 comprises a sleeve 103 for assisting the dental practitioner in making a hole 110 for mounting an implant at a desired location. It shall be appreciated that the guide 102 in these views is shown as a virtual representation which can be adjusted by the user as per specific requirements. A physical component corresponding to the finished design can thus be produced e.g., using a CAM system by providing a processed digital dental impression for machining.

The surgical guide 102 is envisaged to be resting on a portion of the dentition of the patient, which is shown as shaded regions 104 and 105. Any of the shaded regions 104 and 105 may be expanded or shrunk by the user during the design phase to adjust, e.g., the dimensions of the surgical guide 102. Each of the shaded regions 104 and 105 comprises a boundary which encloses the respective region. For example, first shaded region 104 is contained within a first boundary 106, and the second shaded region 105 is contained within a second boundary 107. The term "shaded" region in the present disclosure may also be considered as a "drawing" region, so being shaded or not is not a requirement. Preferably the user should be able to distinguish the region which is relevant for a dental procedure. The shaded regions 104 and 105 thus represent regions, e.g., parts of oral anatomy, which are relevant for a dental procedure. The dental procedure in the context of this example, for instance, can be a procedure of mounting a surgical guide. Hence, the shaded regions can even represent regions which are to be included for a dental procedure. The procedure to which any shaded region is relevant may be the same or it may be different. Thus, different shaded regions may be relevant for different procedures. The region 111 surrounding the shaded regions 104 and 105 may be called unshaded region. The unshaded region 111 may be representative of a part or parts, e.g., of the oral anatomy, which is/are not relevant for a dental procedure.

It shall be appreciated that the views 1(A) and 1(B) represent different perspectives of comparable digital dental impressions (the anatomical variations between 1(A) and 1(B) can be ignored for explanatory purposes without affecting the scope or generality of the present teachings), shown in FIG. 1 with different detail. For example, the guide 102 is not visible in the view 1(B), for example at the command of the user to just view the shaded regions 104 and 105. Hence, the image of the digital dental impression may be altered as per the command of the user. For example, the user may prefer to rotate the digital impression to view the impression from another angle. Accordingly, the image may be updated to visualize the impression from the another angle. The shaded regions 104 and 105, and the unshaded region 111 are also adapted according to the another angle, e.g., for the user to check if the coverage of the regions is as desired. The dental impression may be in the form of one or more datasets. The digital dental impression may be captured for example, via a scan of the patient's anatomy.

Figure 2:
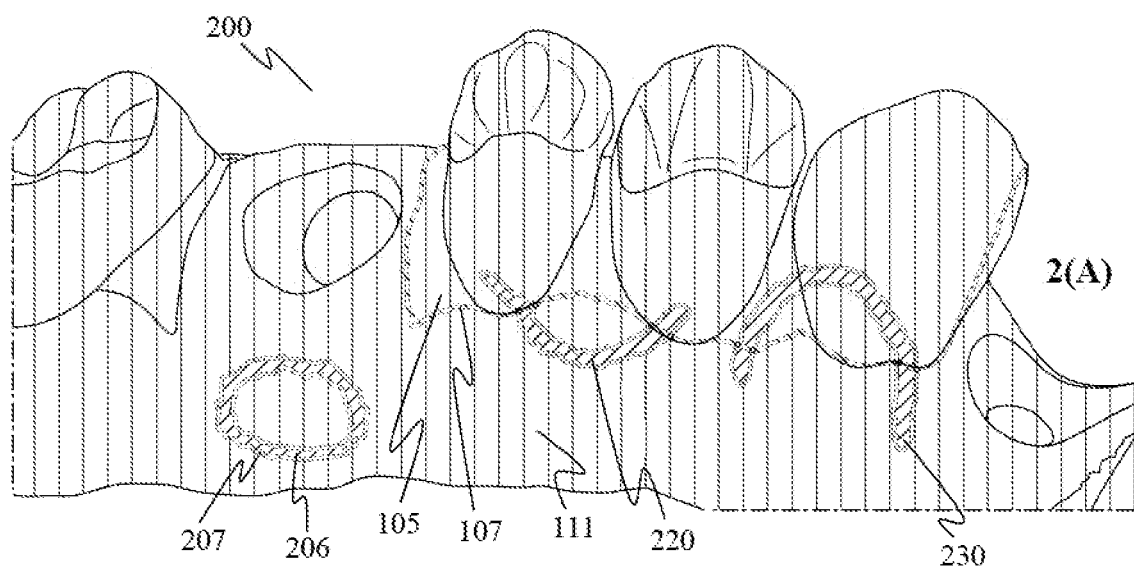
FIG. 2 illustrates certain strokes that may be made during the design of the surgical guide.
Figure 2:
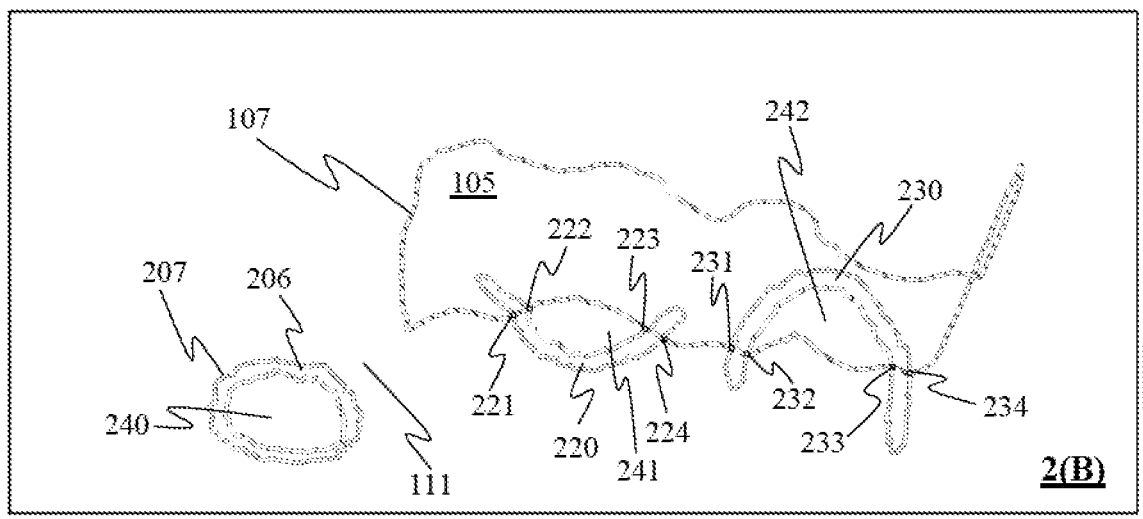
Figure 2:
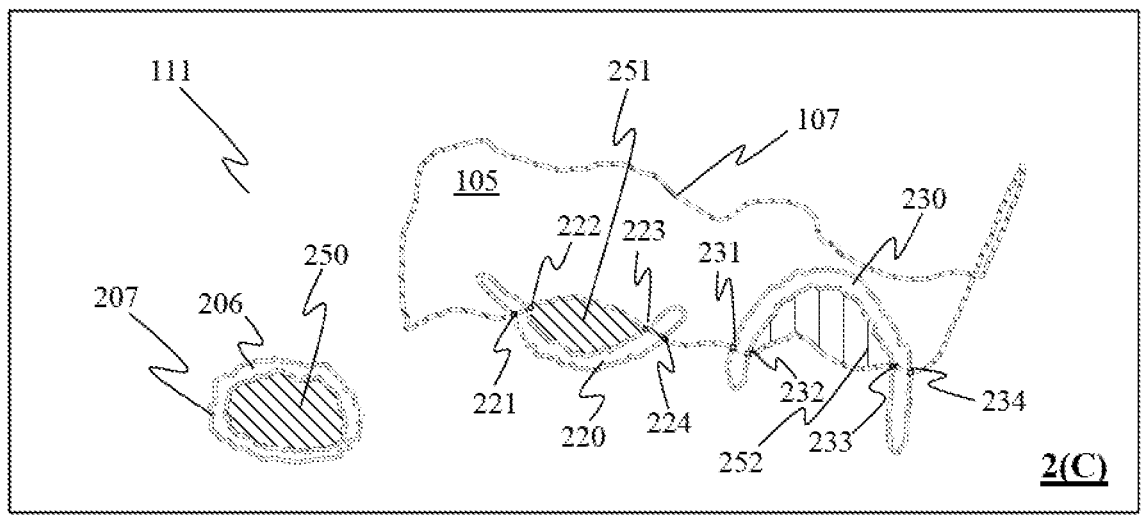

FIG. 2 illustrates alternative views 200 of the digital dental impression, now also showing examples of certain strokes that may be made by the user. The first view 2(A) is similar to the view 1(B) shown in FIG. 1. It is shown a first stroke 220, a second stroke 230 and a third stroke 206. The first stroke 220 may be a kind of stoke that is made to draw Or expand a shaded region, in this case the second shaded region 105. The second stroke 230 is a kind of stroke that is made to erase or shrink a part of the second shaded region 105. The third stroke 206 is a self-intersecting stroke, which may be used for drawing a new shaded region in the unshaded region 111. As it can be seen, each stroke has a width which may correspond to the brush or eraser width that the user has selected for drawing or erasing respectively. The brush width in some cases may correspond to the size of the user's finger, for example, when a touchscreen input device is used for inputting the strokes. Some drawing applications offer width adaptation according to the pressure that the user exerts while drawing specific parts of the sketch. The width may either be constant over the length of the stroke, or it may be variable. Each stroke also has a length which corresponds to the longest dimension along the trail of the stroke. For example, for the third stroke 206, the length approximately would be the circumference of the stroke 206 close to the external outline 207. Due to width of the stroke, each stroke has an outline, which is a perimeter around the stroke.

The view 2(B) shows just the region layer and the strokes. The view 2(B) may thus be a view in which just the region layers and/or stroke layers are visible. It can be seen that the brush stroke 220 intersects the boundary 107 of the second shaded region 105 at two locations. At one location, the outline of the brush stroke 220 intersects the boundary 107 at a first intersection point 221 and a second intersection point 222. At the other location the outline of the brush stroke 220 intersects the boundary 107 at a third intersection point 223 and a fourth intersection point 224. These intersection points 221, 222, 223 and 224 are according to an aspect of the present teachings divided into intersection pairs for detecting whether an enclosed region is formed as a result of the stroke. These aspects will be discussed with reference to the later drawings. Notably, here it can be seen that a first enclosed region 241 is indeed formed. The first enclosed region 241 is enclosed between a part of the outline of the first stroke 220 and a section or part of the boundary 107. More specifically, first enclosed region 241 is enclosed between the part of the outline between the second intersection point 222 and the third intersection point 223 and the section or part of the boundary 107 between the second intersection point 222 and the third intersection point 223. Thus, the first enclosed region 241 comprises a perimeter that is formed by the outline of the first stroke 220 and the section or part of the boundary 107 between the second intersection point 222 and the third intersection point 223.

According to an aspect intersection of the brush stroke 220 with the shaded region 105 is used as a trigger to execute certain algorithms, e.g., a fill-hole algorithm. According to a more preferable aspect, detection of the first enclosed region 241 is used as a trigger to execute one or more algorithms. The detection of enclosed region can either be executed continuously, or intermittently, or it may also be trigger-based. For example, according to another preferable aspect, intersection of the brush stroke 220 with the shaded region 105 may be used as a trigger to execute the enclosed region detection or hole detection logic, and a positive detection of an enclosed region can then be used as a trigger for the fill-hole logic. For example, in response to the detection of the first enclosed region 241, said region may be altered, for example, filled with a first filling 251. The first filling 251 may be the same color as the brush color used for drawing the first stroke 220. The alteration or filling 251 can thus be made automatically without user intervention. In addition, processing intensive algorithms can be prevented from being executed unless they are really needed.

Similarly, the erase stroke 230 intersects the boundary 107 of the second shaded region 105 at two locations. At one location, the outline of the erase stroke 230 intersects the boundary 107 at a first erase intersection point 231 and a second erase intersection point 232. At the other location the outline of the erase stroke 230 intersects the boundary 107 at a third erase intersection point 233 and a fourth erase intersection point 234. These intersection points 231, 232, 233 and 234 are according to an aspect of the present teachings also divided into intersection pairs for detecting whether an enclosed region is formed as a result of the stroke. It can be seen that a second enclosed region 242 is indeed formed. The second enclosed region 242 is enclosed between a part of the outline of the erase stroke 230 and a section or part of the boundary 107. More specifically, second enclosed region 242 is enclosed between the part of the outline between the second erase intersection point 232 and the third erase intersection point 233 and the section or part of the boundary 107 between the second erase intersection point 232 and the third erase intersection point 233. Thus, the second enclosed region 242 comprises a perimeter that is formed by the outline of the second stroke 230 and the section or part of the boundary 107 between the second erase intersection point 232 and the third erase intersection point 233.

According to an aspect, intersection of the erase stroke 230 with the shaded region 105 is used as a trigger to execute certain algorithms, e.g., a remove fill algorithm and, or fill-hole algorithm. According to a more preferable aspect, detection of the second enclosed region 242 is used as a trigger to execute one or more algorithms. The detection of enclosed region can either be executed continuously, or in or it may also be trigger-based. For example, according to another preferable aspect, intersection of the erase stroke 230 with the shaded region 105 may be used as a trigger to execute the enclosed region detection logic, and a positive detection of an enclosed region can then be used as a trigger for the erase-island logic, e.g., erase-fill or remove-island algorithm. For example, in response to the detection of the second enclosed region 242, said region may be altered, for example, filling removed 252 or perhaps filled with a different color. The alteration or filling removal 252 can thus be made automatically without user intervention. In addition, processing intensive algorithms can be prevented from being executed unless they are really needed.

In the case of the self-intersection stroke 206, similar approach can be used by using self-intersection of the stroke as a trigger, either to fill-hole and/or trigger detection of enclosed space, or even for removal of an island of shaded region using remove-filling. The self-intersection stroke 206 is an example of how isolated shaded regions may be created quickly. The user draws the self-intersection stroke 206, when the stroke is completed, a third enclosed region 240 is detected. Upon detection, other algorithms, such as a fill-hole algorithm is executed and a third fill 250 applied within the inner outline of the self-intersecting stroke. As a result, the user can quickly create new shaded regions which are relevant for a dental procedure by just defining the outer outline of the region. Similarly, quick erasures can be made.

According to a preferable aspect, the filling is promptly visualized in response to automatically detecting an enclosed region such that the user may appreciate a possible end result. Due to faster response due to the present teachings, this can be done even before the stroke is finished, or while the user is still drawing.

Figure 3:
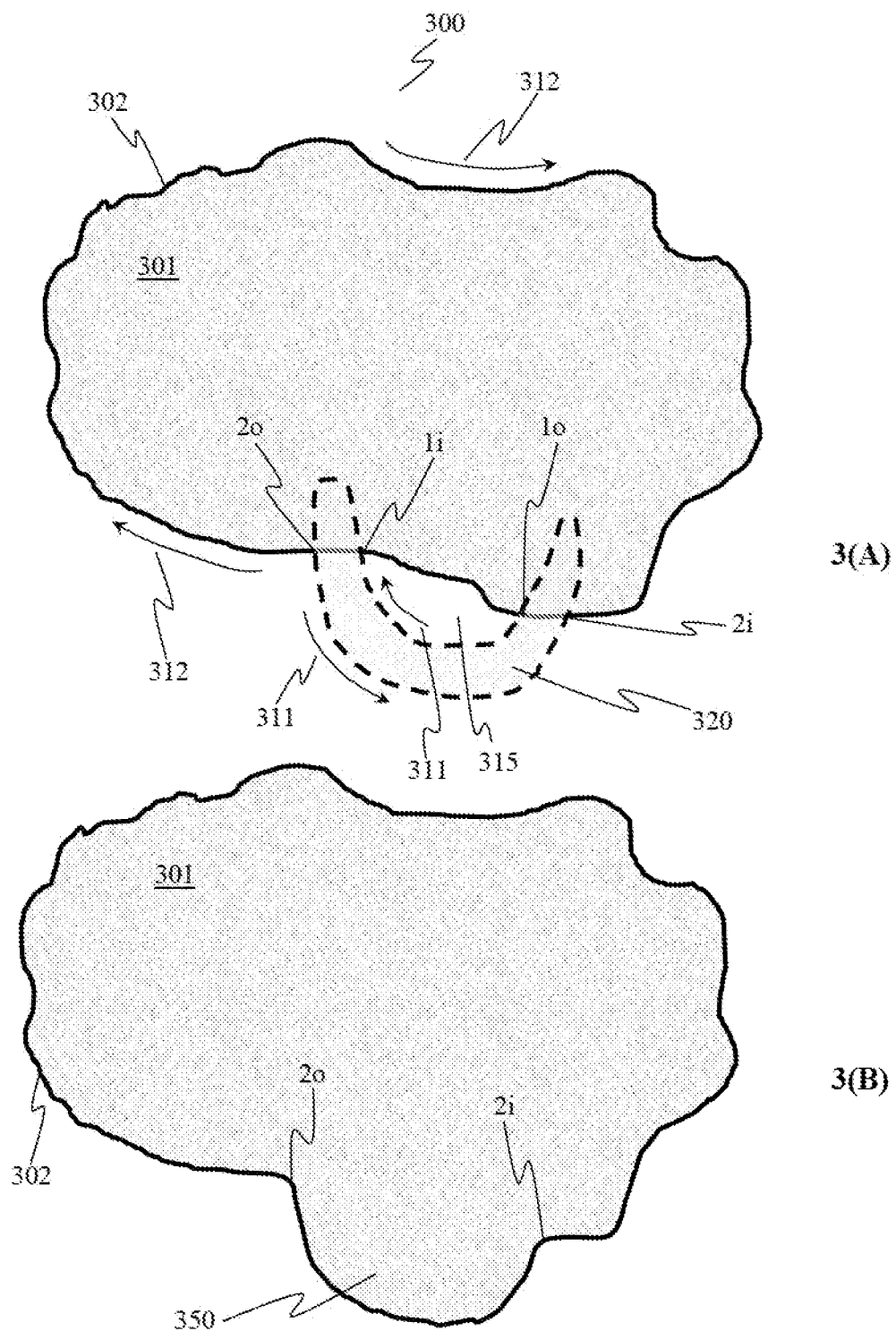
FIG. 3 illustrates detection of enclosed regions with draw or brush strokes.

Now, with reference to FIG. 3 it will be shown an example 300 of detection of enclosed region. It is shown a shaded region 301 which may represent region of interest in a digital 3D anatomical impression. The shaded region 301 is defined or enclosed by a boundary or boundary line 302. The region outside of the boundary 302 is unshaded region. A brush stroke 320 is shown drawn for expanding the shaded region 301. Accordingly, the brush color is similar or same as the color of the shaded region 301. As can be seen, the outline of the brush intersects the boundary 302 such that four intersection points $1i$, $1o$, $2i$ and $2o$ are created. Assuming a first direction 311, which is counterclockwise in this example, it can be seen that the points $1i$ and $2i$ correspond to incoming edges of the stroke 320, i.e., along the first direction 311, the stroke outline "enters" the shaded region 301. Similarly, the points $1o$ and $2o$ correspond to outgoing edges of the stroke 320, i.e., the stroke outline "leaves" the shaded region 301.

For forming intersection pairs, two consecutive intersection points starting from any outgoing edge are allocated to a given intersection pair. For example, starting, from point $1o$, which is an outgoing intersection, the next intersection in the first direction 311 is the point $1i$. Hence, the points $1o$ and $1i$ form a first intersection pair. Continuing along the same path, the next point is $2o$, followed by $2i$, which then become a second intersection pair.

For calculating the distance d for any intersection pair, one can start from the outgoing edge of the pair and measure a distance, along the boundary 302 in a section determination direction 312, until the second point or its incoming edge is reached. For example, for the first intersection pair, starting from $1o$ and moving along the boundary 302 in the section determination direction 312, the distance value would be the section length of the boundary 302 until one reaches the incoming edge point $1i$ of the first intersection pair. As can be seen, this length d would be a small fraction of the total length L of the boundary 302. In contrast, for the second intersection pair, starting from the point $2o$, in the section determination direction 312, one measures the majority of length of the entire length L until reaching the other point $2i$. By using an appropriate value of x in equation (1), distance d of the second pair can be rejected, while the distance d of the first intersection pair would meet the criteria, for example, that d should be less than or equal to 30% of L for a positive enclosed space detection.

$$d \le \frac{L}{x} \quad (1)$$

As it will be noticed, the above example meets the criteria set out in (2), i.e., $$d = \begin{cases} d_{o \to i}, & \text{if section determination direction} \ne \text{the first direction} \\ d_{i \to o}, & \text{if section determination direction} = \text{the first direction} \end{cases} \quad (2)$$

Similar result can be achieved by starting from point 2o rather than from 1o for initiating forming intersection pairs. Also, similar results can be achieved if the first direction is clockwise while the section determination direction is counterclockwise. Moreover, similar results can be achieved if both the first direction and the section determination direction are clockwise, or even if both are counterclockwise. If both directions are the same, then measurement direction can be reversed. Hence, any implementation would work until it satisfies the criteria (2).

The advantage of the approach will become more apparent in the following, as it also allows determining when no valid enclosed region is formed. Hence, improving triggering of the algorithms which should only run when needed.

As it can be seen in the view 3(B), the shaded region 301 is expanded and the enclosed space 315 auto filled 350. Location of the intersection points 2i and 2o is provided as a reference.

Figure 4:
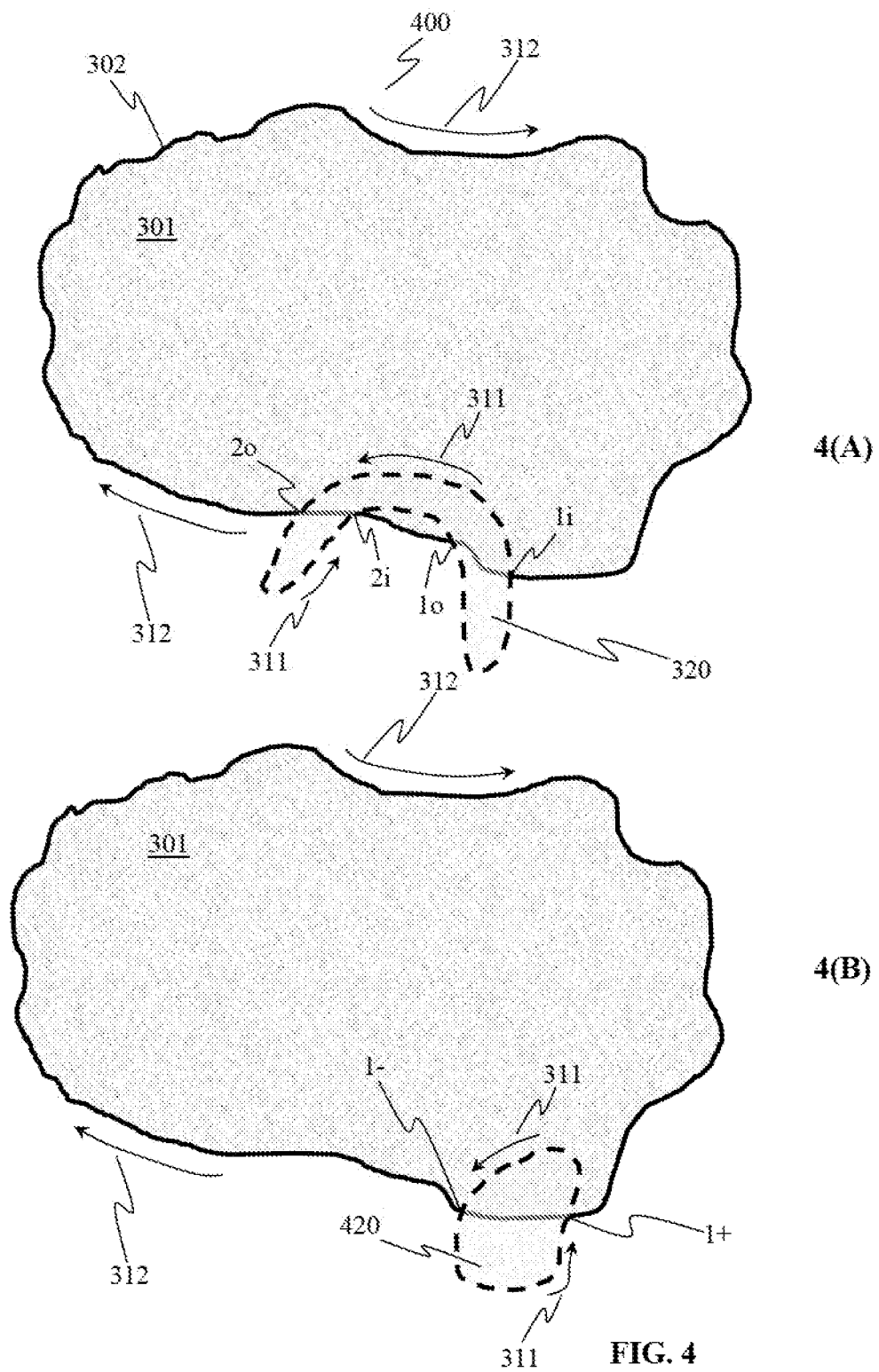
FIG. 4 illustrates rejection of invalid enclosed regions with draw or brush strokes.

Now, with reference to FIG. 4 it will be shown an example 400 of how false detection of enclosed region is rejected h the present teachings. The first view 4(A) shows a brush stroke 320 which is made into the shaded region 301. As can be seen, there is no enclosed region, or a hole of unshaded region enclosed between the stroke 320 and the shaded region 301 (e.g., unlike region 315 as shown in FIG. 3). In this case, there is no need to perform a hole fill algorithm. Following similar criteria as discussed in context of FIG. 3, starting from an outgoing edge, e.g., 1o, a first intersection pair is 1o and 1i and the second intersection pair is 2o and 2i. As it can be seen, when starting from the outgoing edge of any of the pairs and moving along the section determination direction 312, distance value d would be very high, in this example close to the complete length L of the boundary 302. Thus, using equation (1), none of the distance values would indicate an enclosed region, hence no processing intensive algorithms such as fill hole needs to be executed.

Similarly, for a brush stroke which more resembles a tap 420 rather than a draw stroke, as shown in 4(B), there will be only one edge pair as there is a single intersection location. To distinguish from the intersection pairs of other drawings an alternative natation is used here. The single intersection pair is formed by an outgoing edge point 1− and an incoming edge point 1+. Similar to the previous discussions, the distance value d here would also be very high, and hence no valid enclosed region is detected.

As discussed previously, the criteria would work even if other directions or notation s are used as long as they generally meet criteria (2).

Figure 5:
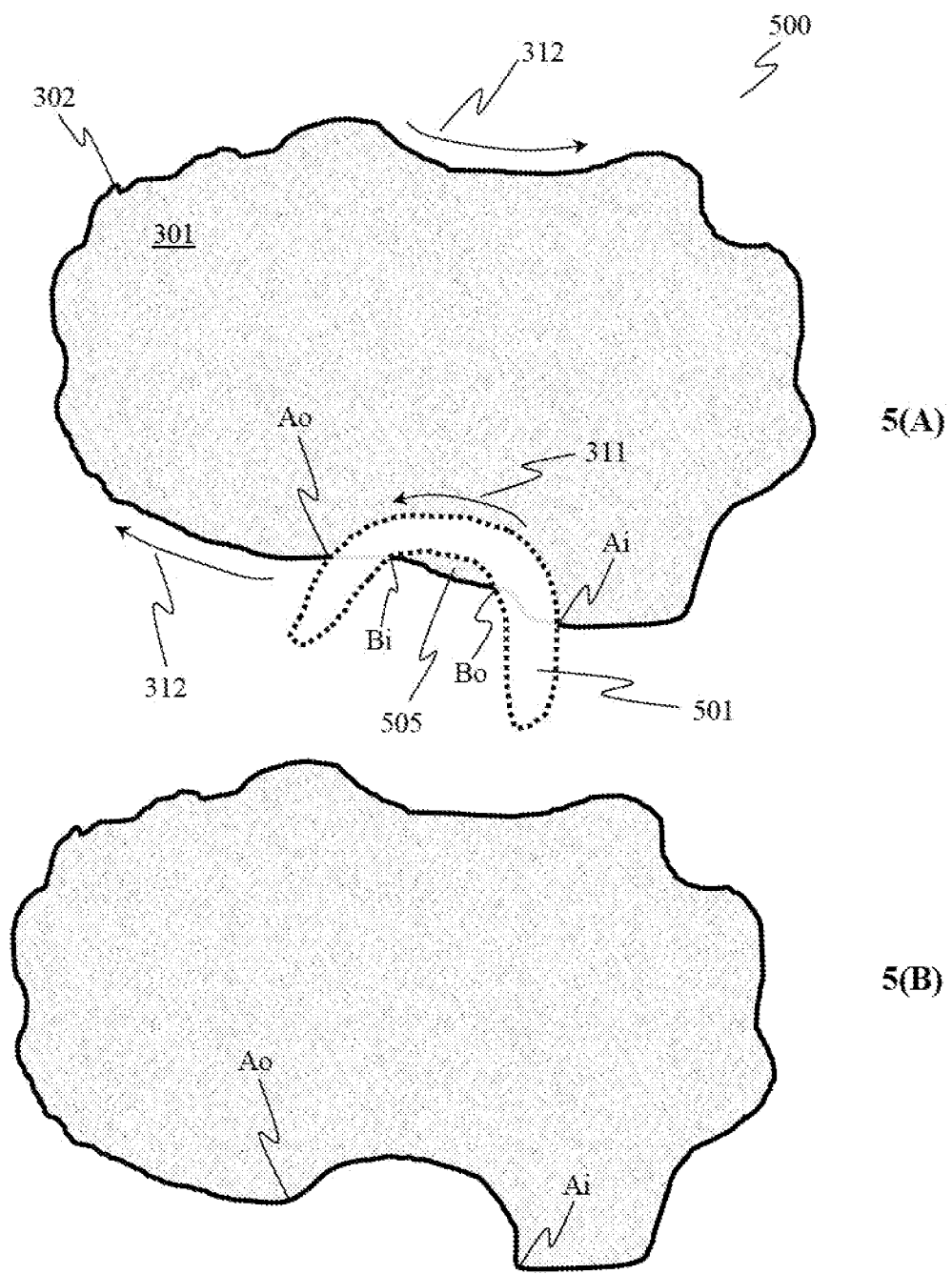
FIG. 5 illustrates detection of enclosed regions with erase strokes.

Now, with reference to FIG. 5 it Will be shown an example 500 of how the present teachings can also be applied to erase strokes. In view 5(A), an erase stroke 501 is shown made into the shaded region 301. The outline of the stroke 501 intersects the boundary 302 at intersection points Ao, Ai, Bo and Bi. An enclosed region 505 has been formed as a result of the stroke 501. It would conventionally require a manual erasure or alteration. As a slight variation to the draw or brush approach discussed in previous figures, intersection pairs are formed starting from incoming (or positive) intersections, instead of from outgoing or (negative) intersections. Hence, moving along the first direction 311, and starting from any incoming edge, e.g., Ai, a first intersection pair would have points Ai and Ao while a second intersection pair would have points Bi and Bo. For calculating distance d for each of the respective pairs, we in this example start from an outgoing edge (because the section determination direction ≠ the first direction). As can be seen, for Ai and Ao, the distance value would be very large, while for the pair Bi and Bo, it would satisfy equation (1).

It should be noted that instead of directly using equation (1), one could also form other criteria, such as adding the two distance values for the two pairs and check if the sum is closer to L. For example, the two distance values plus the width of the stroke at the intersection should be exactly or essentially equal to L. For a no valid enclosed region case, the sum of lengths would tend to have a larger difference from L. Similarly, other criteria can be envisaged. An advantage of calculating the distance value d for each pair can be that it also gives an indication of where the enclosed region is formed. As can be seen, the enclosed regions form between the intersection pairs that satisfy criteria similar to equation (1).

The second view 5(B) shows how the enclosed region 505 has been automatically erased in response to the enclosed region detection. Points Ao and Ai are shown just for reference.

As it was discussed in context of draw strokes in FIG. 4 it will be appreciated that pursuant to the present teachings, in a similar manner, false detection of enclosed region is also prevented in erase strokes. Hence, an erase stroke of a similar form as the brush stroke 320 shown in the view 3(A) can be shown to be providing a negative detection of enclosed region. Similarly, an erase stroke of similar form as the brush stroke 420 as shown in the view 4(B) can also be shown to provide a negative detection of enclosed region by following a trigger approach which satisfies the criteria defined in (1) and (2).

Figure 6:
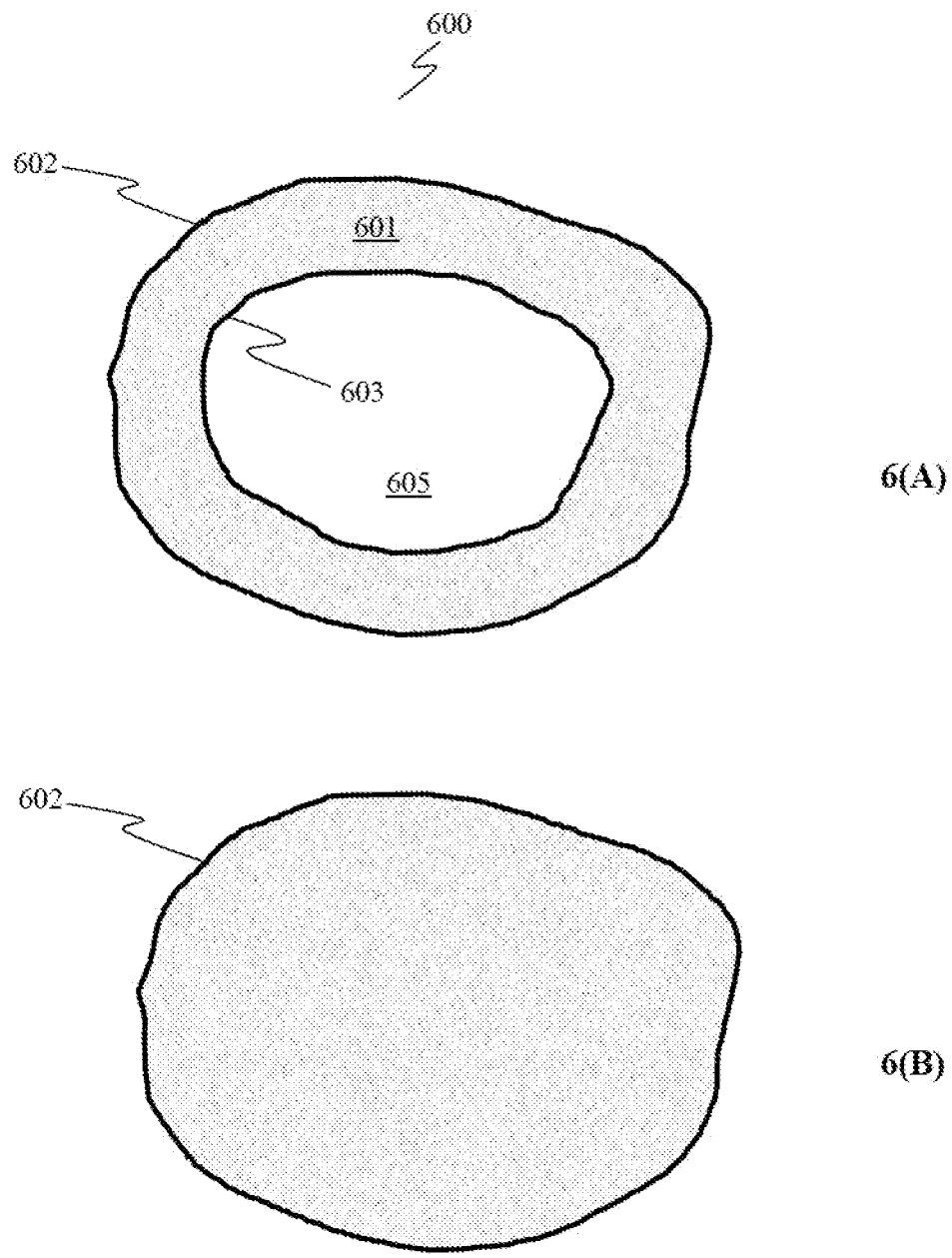
FIG. 6 illustrates a self-intersecting stroke.
Figure 7:
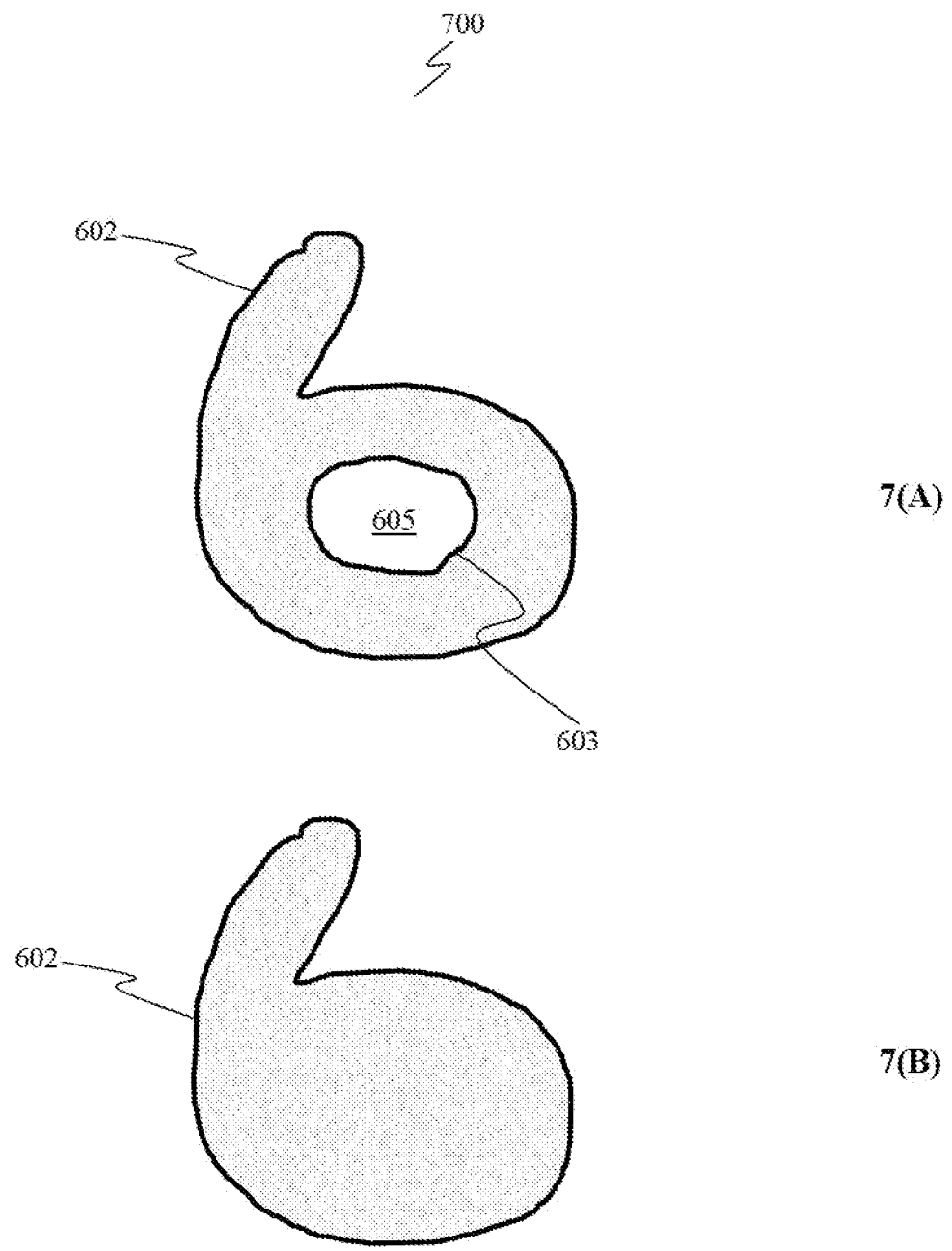
FIG. 7 illustrates another self-intersecting stroke.

FIGS. 6 and 7 illustrates examples 600 and 700 of self-intersecting strokes. Such a stroke can be made for example, when the user draws as loop. Due to intersection of the leading end of the stroke with its trail, the loop is formed. Traditionally, as shown in 6(A) and 7(A), an enclosed space 605 would be formed which would need to be filled. Pursuant to the present teachings, a stroke completion may be detected, which can be triggered by an intersection of one or more points of the stroke. In response to which, should an internal outline 603 be formed, another algorithm such as a fill-hole algorithm may be executed. More preferably, the stroke completion is detected by the formation of the second outline 603. The end result can be as seen in 6(B) and 7(B) respectively, where the internal outline 603 is auto filled, thus filling the hole with a fill corresponding to a shaded region. Hence, a shaded region with a boundary 602 is formed by the outer outline of the stroke. This can speed up the formation of regions relevant for processing.

Figure 8:
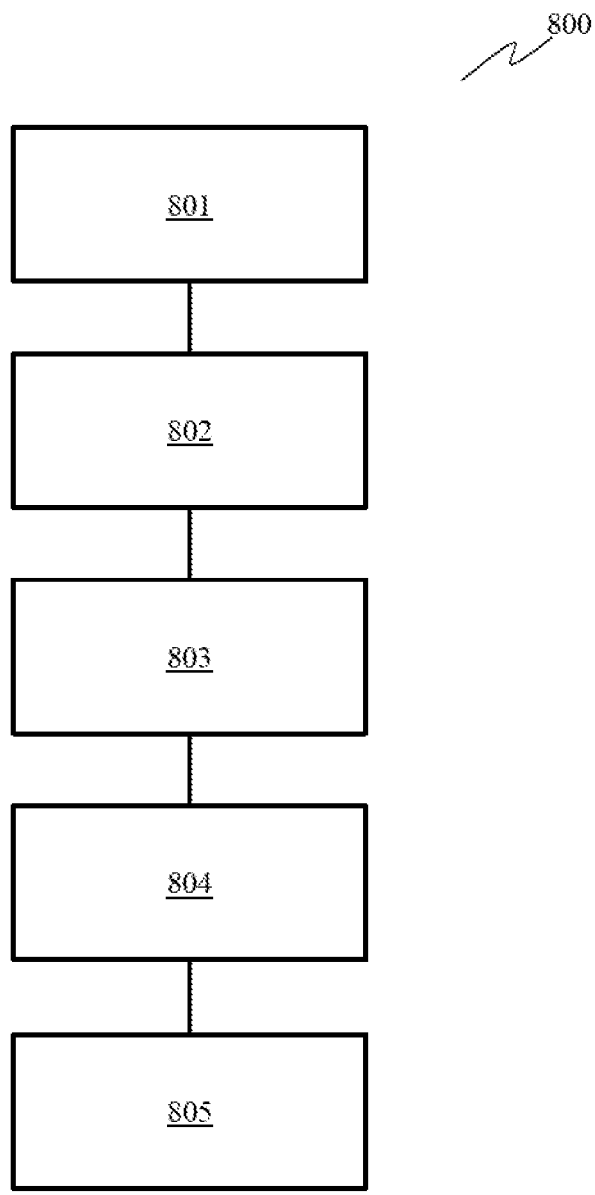
FIG. 8 is a flowchart showing a method aspect of the present teachings.

FIG. 8 illustrates a flowchart or routine 800 for processing a digital dental, impression as also discussed in the preceding FIGS. The routine 800 may be executed by any one or more suitable computing units or by a dental procedure assisting system.

In block 801, it is provided, the digital dental impression. The digital dental impression may for example be obtained by operatively connecting to a memory location, or it may be generated e.g., via a scan. In block 802, it is displayed via a display device, an image of the digital dental impression. The image may comprise one or more shaded regions. The shaded region may be representative of a part of the oral anatomy which is relevant for a dental procedure. The shaded region may be enclosed within a boundary. The image may also comprise an unshaded region. The unshaded region may be representative of a part of the oral anatomy which is not relevant for a dental procedure. The unshaded region and the shaded region are separated from each another by the boundary. In block 803, it is received via an input interface, a user input for altering the shaded region and/or unshaded region. In block 804, it is detected, via, a trigger logic, completion of a stroke generated by the user input. In block 805, the shaded region and/or the unshaded region are altered in response to the stroke completion.

Figure 9:
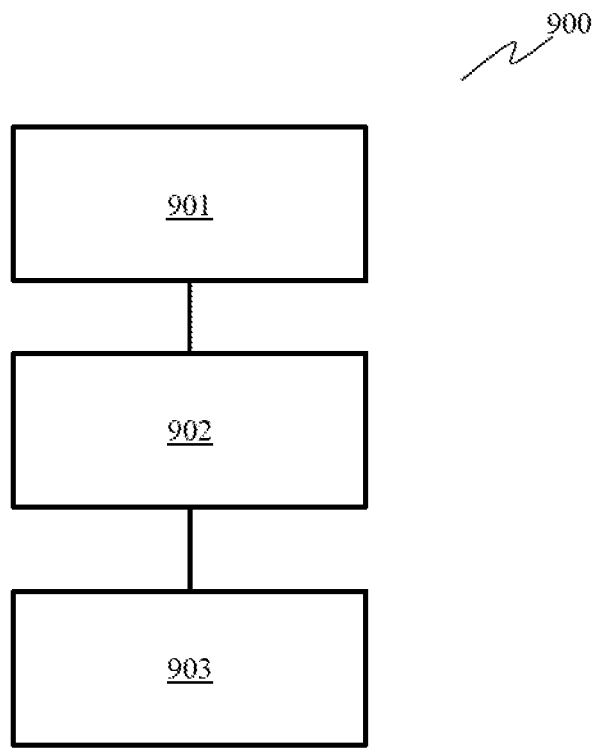
FIG. 9 illustrates another flowchart showing another method aspect.

FIG. 9 illustrates a further flowchart or another routine 900 for method for processing digital three-dimensional shapes, which may be implemented as trigger logic. The another routine 900 may be a part of the routine 800, e.g., as was shown in the block 804, or it may be a standalone routine for processing digital three-dimensional shapes, for example, in another location or by another computing unit. Those skilled in the art shall appreciate that the present teachings can be advantageously leveraged for other kinds of 3D shapes besides dental geometries.

In block 901, it is detected intersection of a drawing stroke at a boundary at two different locations of the boundary. The boundary separates a digital geometrical surface from a vacant digital canvas space. The digital geometrical surface may be called a shaded area, while the vacant canvas may be called an unshaded area. In block 902, it is detected via any one or more of the computing units, an enclosed region formed by the drawing stroke and the section of the boundary between the two intersection locations. In block 903, properties of the shaded region are altered via any one or more of the computing units. Optionally, the enclosed region may be partially confined by a section of a boundary which separates a shaded region from an unshaded region. The enclosed region may be confined within the section and the outline, and the new boundary may also include the section.

The method steps may be performed in the order as shown listed in the examples or aspects. It should be noted, however, that under specific circumstances a different order may also be possible. Further, it is also possible to perform one or more of the method steps once or repeatedly. These steps may be repeated at regular or irregular time periods. Further, it is possible to perform two or more of the method steps simultaneously or in a timely overlapping fashion, specifically when some or more of the method steps are performed repeatedly. The method may comprise further steps which are not listed.

The word "comprising" does not exclude other elements or steps, and the indefinite article "a" or "an" does not exclude a plurality. A single processing means, processor or controller or other similar unit may fulfill the functions of several items recited in the claims. The mere fact that certain measures are recited in mutually different dependent claims does not indicate that a combination of these measures cannot be used to advantage. Any different signs in the claim should not be construed as limiting the scope.

Further, it should be noted that in the present disclosure, the terms "at least one", "one or more" or similar expressions indicating that a feature or element may be present once or more than once typically may have been used only once when introducing the respective feature or element. Thus, in some cases unless specifically stated otherwise, when referring to the respective feature or element, the expressions "at least one" or "one or more" may not have been repeated, notwithstanding the fact that the respective feature or element may be present once or more than once.

Further, the terms "preferably", "more preferably", "particularly", "more particularly", "specifically", "more specifically" or similar terms are used in conjunction with optional features, without restricting alternative possibilities. Thus, any features introduced by these terms are optional features and are not intended to restrict the scope of the claims in any way. The present teachings may, as those skilled in the art will recognize, be performed by using alternative features. Similarly, the features introduced by "according to one aspect" or similar expressions are intended to be optional features, without any restriction regarding alternatives to the present teachings, without any restrictions regarding the scope of the present teachings and without any restriction regarding the possibility of combining the features introduced in such way with other optional or non-optional features of the present teachings.

Unless otherwise defined, all technical and scientific terms used herein have the same meaning as commonly understood by one of ordinary skill in the art to which the present teachings belong.

Various examples have been disclosed above for a method, a system, a device, a use, software program, and a computing unit comprising the computer program code for carrying out the methods herein disclosed. For example, it has been disclosed a method for processing a digital dental impression comprising:—displaying an image of the digital dental impression; wherein the image comprises: a shaded region representative of a part of the oral anatomy which is relevant for a dental procedure, and the shaded region being enclosed within a boundary; and an unshaded region representative of a part of the oral anatomy which is not relevant for a dental procedure, wherein the unshaded region and the shaded region are separated from each another by the boundary, —receiving user input for altering the shaded region and/or unshaded region; —detecting completion of a stroke generated by the user input; —altering, the shaded region and/or the unshaded region, in response to the stroke completion. The present teachings also relate to a method for processing digital three-dimensional shapes, a dental procedure assisting system, uses and computer software products. Those skilled in the art will understand however that changes and modifications may be made to those examples without departing from the spirit and scope of the accompanying claims and their equivalence. It will further be appreciated that aspects from the method and product embodiments discussed herein may be freely combined.

Any headings utilized within the description are for convenience only and have no legal or limiting effect.

It shall be clear to those skilled in the art that when referring to embodiments in the claims or clauses, statements such as "any of the claims a-b", mean "any one or more of the claims a, b, and/or any of the claims that lie in between a and b". Thus, "any of the claims a-b" is supposed to specify embodiments which include the features of: claim a and/or claim b and/or any one of the claims between a and b and/or any combination of any two or more the claims from a until b; a and b being respective claim numbers.

Summarizing and without excluding further possible embodiments, certain example embodiments of the present teachings are summarized in the following clauses:

Clause 1. A computer-implemented method for processing a digital dental impression, the digital dental impression being representative of an oral anatomy, which method comprises:
   providing, at a memory location, the digital dental impression;
   displaying, via a display device, an image of the digital dental impression; herein the image comprises:
      a shaded region, the shaded region being representative of a part of the oral anatomy which is relevant for a dental procedure, and the shaded region being enclosed within a boundary; and an unshaded region, the unshaded region being representative of a part of the oral anatomy which is not relevant for a dental procedure, wherein the unshaded region and the shaded region are separated from each another by the boundary, receiving, via an input interface, a user input for altering the shaded region and/or unshaded region;

detecting, via a trigger logic, a transition of the user input between the shaded region and the unshaded region;

altering the shaded and/or unshaded region, in response to the transition which crosses the boundary at least twice.

Clause 2. A computer-implemented method for processing a digital dental impression, the digital dental impression being representative of an oral anatomy, which method comprises:

providing, at a memory location, the digital dental impression;

displaying, via a display device, an image of the digital dental impression; wherein the image comprises:

a shaded region, the shaded region being representative of a part of the oral anatomy which is relevant for a dental procedure, and the shaded region being enclosed within a boundary; and an unshaded region, the unshaded region being representative of a part of the oral anatomy which is not relevant for a dental procedure, wherein the unshaded region and the shaded region are separated from each another by the boundary, receiving, via an input interface, a user input for altering the shaded region and/or unshaded region;

detecting, via a trigger logic, completion of a stroke generated by the user input;

altering, the shaded region and/or the unshaded region, in response to the stroke completion.

Clause 3. Method according to any of the clauses 1 or 2, wherein the method also comprises:

generating a processed digital dental impression based upon the digital dental impression, the processed digital dental impression including information of the altered shaded region and; or the altered unshaded region.

Clause 4. Method according to clause 3, also comprising:
performing, using the processed digital dental impression, a dental procedure.

Clause 5. Method according to clause 3, also comprising:
manufacturing, using the processed digital dental impression, a dental object.

Clause 6. Method according to clause 4, wherein the dental object is a surgical guide.

Clause 7. Method according to clause 4, wherein the dental object is a crown.

Clause 8. Method according to clause 4, wherein the dental object is a bridge.

Clause 9. Method according to any of the above clauses, wherein the altering of the unshaded region involves performing a filling operation in an enclosed region at least partially enclosed by the stroke.

Clause 10, Method according to any of the above clauses 1-8, wherein the altering of the shaded region involves performing an erase operation in an enclosed region at least partially enclosed by the stroke.

Clause 11. Method according to any of the above clauses, wherein the stroke completion is detected by an intersection of the stroke either by itself or with the shaded region, preferably at two locations.

Clause 12. Method according to any of the above clauses, wherein a fill-hole algorithm is executed in response to the stroke completion.

Clause 13. Method according to any of the above clauses, wherein the stroke completion detection involves determination of formation of an enclosed region.

Clause 14. Method according to clause 13, wherein the determination of formation of the enclosed region involves computation of distances between the intersection points of outline of the stroke and the boundary.

Clause 15. Method according to clause 14, wherein the distance calculation involves formation of one or more intersection pairs, each pair formed by two adjacent intersection points.

Clause 16. Method according to clause 15, wherein each intersection pair is formed by starting from an outgoing intersection point.

Clause 17. Method according to clause 15, wherein each intersection pair is formed by starting from an incoming intersection point.

Clause 18. A system for assisting a dental procedure, wherein e system is configured to perform the steps of any of the above method clauses.

Clause 19. A dental procedure assisting system, wherein the system is configured to:

operatively connect to a memory location for obtaining a digital dental impression, wherein the digital dental impression is representative of an oral anatomy;

display, via a display device, an image of the digital dental impression; wherein the image comprises:

a shaded region, the shaded region being representative of a part of the oral anatomy which is relevant for a dental procedure, and the shaded region being enclosed within a boundary; and an unshaded region, the unshaded region being representative of a part of the oral anatomy which is not relevant for a dental procedure, wherein the unshaded region and the shaded region are separated from each another by the boundary;

receive, via an input interface, a user input for altering the shaded region and/or unshaded region;

detect, via a trigger logic, completion of a stroke generated by the user input;

alter, the shaded region and/or the unshaded region, in response to the stroke completion.

Clause 20. A computer software product, or a non-transitory computer-readable storage medium storing the program, comprising instructions which when executed by a suitable computing unit cause the computing unit to perform the steps of any of the above method clauses.

Clause 21. A trigger logic for processing digital three-dimensional (3D) shapes, specifically digital anatomical shapes, wherein the logic is configured to:

detect completion of a stroke; wherein the completion of the stroke involves forming of an enclosed region confined at least partially within an outline of the stroke, create a new boundary around the enclosed region; the new boundary including the outline, alter properties of the enclosed region.

Clause 22. Trigger logic according to clause 12, wherein the enclosed region is partially confined by a section of a boundary which separates a shaded region from an unshaded region, and wherein the enclosed region is confined within the section and the outline, and wherein the new boundary also includes the section.

Clause 23. A trigger logic for processing digital three-dimensional (3D) drapes, specifically digital anatomical shapes, wherein the logic is configured to:

detect intersection of a drawing stroke at a boundary at two different locations of the boundary; wherein the boundary separates a shaded region from an unshaded region, detect an enclosed region formed by the drawing stroke and the section of the boundary between the two intersection locations, alter properties of the shaded region.

Clause 24. Use of the processed digital dental impression as generated in clause 3 for producing a dental object.

Clause 25. A data storage medium storing the processed digital dental impression as generated in clause 3.

The invention claimed is:

1. A computer-implemented method for processing a digital dental impression to form a dental object, the digital dental impression being representative of an oral anatomy, comprising:

providing, at a memory location, the digital dental impression;

displaying, via a display device, an image of the digital dental impression; wherein the image comprises:

a shaded region, the shaded region being representative of a part of the oral anatomy which is relevant for a dental procedure, and the shaded region being enclosed within a boundary; and an unshaded region, the unshaded region being representative of a part of the oral anatomy which is not relevant for a dental procedure, wherein the unshaded region and the shaded region are separated from each another by the boundary, receiving, via an input interface, a user input for altering the shaded region and/or unshaded region;

detecting, via a trigger logic, completion of a stroke generated by the user input;

altering, the shaded region and/or the unshaded region, in response to the stroke completion;

generating a processed digital dental impression based upon the digital dental impression, the processed digital dental impression including information of the altered shaded region and/or the altered unshaded region, and a computer-aided manufacturing machine configured to manufacture using the processed digital dental impression, the dental object.

2. The method according to claim 1, also comprising:
performing, using the processed digital dental impression, a dental procedure.

3. The method according to claim 1, wherein the dental object is a surgical guide.

4. The method according to claim 1, wherein the altering of the unshaded region involves performing a filling operation in an enclosed region at least partially enclosed by the stroke.

5. The method according to claim 1, wherein the altering of the shaded region involves performing an erase operation in an enclosed region at least partially enclosed by the stroke.

6. The method according to claim 1, wherein the stroke completion is detected by an intersection of the stroke either by itself or with the shaded region.

7. The method according to claim 1, wherein a fill-hole algorithm is executed in response to the stroke completion.

8. The method according to claim 1, wherein the stroke completion detection involves determination of formation of an enclosed region.

9. A system for assisting a dental procedure, comprising a computer with a processor; and a memory storing instructions that, when executed by the processor, configure the system to:

provide, at a memory location, a digital dental impression that is representative of an oral anatomy;

display, via a display device, an image of the digital dental impression; wherein the image comprises:

a shaded region, the shaded region being representative of a part of the oral anatomy which is relevant for a dental procedure, and the shaded region being enclosed within a boundary; and an unshaded region, the unshaded region being representative of a part of the oral anatomy which is not relevant for a dental procedure, wherein the unshaded region and the shaded region are separated from each another by the boundary, receive, via an input interface, a user input for altering the shaded region and/or unshaded region;

detect, via a trigger logic, completion of a stroke generated by the user input;

alter, the shaded region and/or the unshaded region, in response to the stroke completion;

generate a processed digital dental impression based upon the digital dental impression, the processed digital dental impression including information of the altered shaded region and/or the altered unshaded region, and a computer-aided manufacturing machine configured to manufacture, the processed digital dental impression, a dental object.

* * * * *

UNITED STATES PATENT AND TRADEMARK OFFICE
CERTIFICATE OF CORRECTION

PATENT NO. : 12,295,809 B2
APPLICATION NO. : 17/395689
DATED : May 13, 2025
INVENTOR(S) : Kühnel-Sumann et al.

Page 1 of 1

It is certified that error appears in the above-identified patent and that said Letters Patent is hereby corrected as shown below:

In the Claims

In Column 27, Line 44, in Claim 2, delete "also" and insert --further-- therefor In Column 28, Line 46, in Claim 9, before "the", insert --using--

Signed and Sealed this
Eighth Day of July, 2025

Coke Morgan Stewart
*Acting Director of the United States Patent and Trademark Office*